(12) United States Patent
Hotchkiss et al.

(10) Patent No.: US 8,846,978 B2
(45) Date of Patent: Sep. 30, 2014

(54) ELECTRONIC DEVICES COMPRISING NOVEL PHOSPHONIC ACID SURFACE MODIFIERS

(75) Inventors: Peter Hotchkiss, Washington, DC (US); Seth Marder, Atlanta, GA (US); Anthony Giordano, Atlanta, GA (US); Thomas D. Anthopoulos, London (GB)

(73) Assignees: Imperial Innovations Ltd., London (GB); Georgia Tech Research Corporation, Atlanta, GA (US)

( * ) Notice: Subject to any disclaimer, the term of this patent is extended or adjusted under 35 U.S.C. 154(b) by 251 days.

(21) Appl. No.: 13/262,739

(22) PCT Filed: Apr. 2, 2010

(86) PCT No.: PCT/EP2010/054466
§ 371 (c)(1),
(2), (4) Date: Dec. 27, 2011

(87) PCT Pub. No.: WO2010/115854
PCT Pub. Date: Oct. 14, 2010

(65) Prior Publication Data
US 2012/0114974 A1 May 10, 2012

Related U.S. Application Data

(60) Provisional application No. 61/166,877, filed on Apr. 6, 2009.

(51) Int. Cl.
| | | |
|---|---|---|
| C07F 9/08 | (2006.01) | |
| C07F 9/38 | (2006.01) | |
| H01L 51/52 | (2006.01) | |
| H01L 51/00 | (2006.01) | |
| H01L 51/50 | (2006.01) | |

(52) U.S. Cl.
CPC .......... *H01L 51/5203* (2013.01); *C07F 9/3808* (2013.01); *H01L 51/004* (2013.01); *H01L 51/5088* (2013.01)
USPC .................................. 568/11; 568/2; 568/16

(58) Field of Classification Search
CPC ...... C07F 9/3808; C07F 9/3834; H01L 51/56
USPC ............................................... 568/2, 11, 16
See application file for complete search history.

(56) References Cited

U.S. PATENT DOCUMENTS

| | | | |
|---|---|---|---|
| 5,272,035 A | 12/1993 | Sekiya | |
| 8,586,208 B2 * | 11/2013 | Sharma et al. | 428/690 |
| 2005/0239054 A1 | 10/2005 | Arimilli et al. | |
| 2008/0003449 A1 | 1/2008 | Hsu et al. | |
| 2008/0215140 A1 * | 9/2008 | Borck et al. | 623/1.46 |
| 2008/0275273 A1 * | 11/2008 | Effenberger et al. | 568/14 |

FOREIGN PATENT DOCUMENTS

| | | |
|---|---|---|
| DE | 10 2004 057 760 A1 | 6/2006 |
| EP | 0 524 023 A1 | 1/1993 |
| JP | 01-121255 A | 5/1989 |
| WO | WO-2006/124670 A2 | 11/2006 |
| WO | WO-2010/007081 A1 | 1/2010 |
| WO | WO-2010/100194 A1 | 9/2010 |

OTHER PUBLICATIONS

Alloway et al., "Interface Dipoles Arising from Self-Assembled Monolayers on Gold UV-Photoemission Studies of AlkanethiolS and Partially Fluorinated Alkanethiols," J. Phys. Chem. B, 2003, vol. 107, pp. 11690-11699.
Bao, Zhenan, et al. Organic Field-Effect Transistors. Boca Raton, Florida: CRC Press, Taylor & Francis Group, 2007.
Bhattacharya et al., "The Michaelis-Arbuzov Rearrangement," Chem. Rev. 1981, vol. 81, pp. 415-430.
Chempacific Product List #60139, CAS # 1869-27-8- "4-Trifluoromethyl-Phenyl)-Phosphonic Acid," Chemical Book, 2010, 1 page.
Gooβen et al., "Practical Protocol for the Palladium-Catalyzed Synthesis of Arylphosphonates from Bromoarenes and Diethyl Phosphite," Synlett, 2005, vol. 3, pp. 445-448.
Han et al., "High Reactivity of a Five-Membered Cyclic Hydrogen Phosphonate Leading to Development of Facile Palladium-Catalyzed Hydrophosphorylation of Alkenes," J. Am. Chem. Soc., 2000, vol. 122, pp. 5407-5408.
Henderson et al., "Platinum(II) complexes containing ferrocene-derived phosphonate ligands; synthesis, structural characterisation and antitumour activity," Inorgnica Chimica Acta, 2001, vol. 322, No. 2001, pp. 106-112.
Jee et al., "Study on Work Function Change of ITO Modified by Using a Self-Assembled Monolayer for Organic Based Devices," Journal of the Korean Physical Society, 2006, vol. 49, No. 5, pp. 2034-2039.
Khodabakhsh et al. "Using Self-Assembling Dipole Molecules to Improve Hole Injection in Conjugated Polymers," Adv. Funct. Mater., 2004, vol. 14, No. 12, pp. 1205-1210.

(Continued)

*Primary Examiner* — Sudhakar Katakam
*Assistant Examiner* — Pancham Bakshi
(74) *Attorney, Agent, or Firm* — Foley & Lardner LLP

(57) ABSTRACT

In some embodiments, the inventions described herein relate to a composition of matter comprising a molecule having the structure: wherein: independently at each occurrence, $R^1$ is a halogen, a alkyl group, a heteroalkyl group, an aryl group, or a heteroaryl group; $R^2$ comprises from 3 to 30 $CH_2$— groups, n=0-5, m=0-5, q=1-3, and $R^2$ comprises at least one ether linkage.

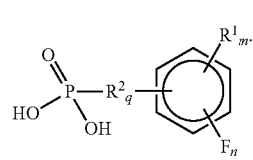

(I)

18 Claims, 24 Drawing Sheets

(56) References Cited

OTHER PUBLICATIONS

Klauk, Hagen. Organic Electronics: Materials, Manufacturing and Applications. Weinheim, Germany: Wiley-VCH Verlag GmbH & Co., KGaA, 2006.

Koh et al., "Phenylphosphonic Acid Functionalization of Indium Tin Oxide: Surface Chemistry and Work Functions," Langmuir, 2006, vol. 22, pp. 6249-6255.

Krecmerova et al., "Preparation of phosphonomethyl ethers derived from 2-phenylethanol and its amino derivatives," Collection of Czechoslovak Chemical Communications, 1995, vol. 60, No. 4, pp. 659-669, XP002588178.

Montoneri et al., "Organosulphor Phosphorus Acid Compounds. Part 4. Fluorobenzylphosphono-Sulphonic Acids," Phosphorous, Sulfur and Silicon and the Related Elements, 1994, vol. 86, No. 1-4, pp. 145-155.

Mullen, Klaus, et al. Organic Light Emitting Devices: Synthesis, Properties and Applications. Weinheim, Germany: Wiley-VCH Verlag GmbH & Co., KGaA, 2006.

Nalwa, Hari Singh. Handbook of Organic Electronics and Photonics: Electronic and Photonic Devices. vol. 3, Stevenson Ranch, California: American Scientific Publishers, 2008.

Nalwa, Hari Singh. Handbook of Organic Electronics and Photonics: Electronic Materials and Devices. vol. 1, Stevenson Ranch, California: American Scientific Publishers, 2008.

Nalwa, Hari Singh. Handbook of Organic Electronics and Photonics: Photonic Materials and Devices. vol. 2, Stevenson Ranch, California: American Scientific Publishers, 2008.

Paniagua et al., "Phosphonic Acid Modification of Indium—Tin Oxide Electrodes: Combined XPS/UPS/Contact Angle Studies," J. Phys. Chem. C, 2008, vol. 112, pp. 7809-7817.

Pfammatter et al., "Synthesis of w-Substituted Alkanethiols and (Bromomethyl)methylthiomalonates," Helvetica Chimica Acta., 2001, vol. 84, No. 3, pp. 678-689.

Rice et al., "Perfluorocarbon Phosphonic and Sulfonic Acids Containing Discretely Varying Terminal Functional Groups," Inorganic Chemistry, 1991, vol. 30, No. 24, pp. 4635-4638.

Sharma et al., "Effect of phosphonic acid surface modifiers on the work function of indium tin oxide and on the charge injection barrier into organic single-layer diodes," Journal of Applied Physics, 2009, vol. 105, No. 074511, pp. 1-6.

Sharma et al., "Tailoring the work function of indium tin oxide electrodes in electrophosphorescent organic light-emitting diodes," Journal of Applied Physics, 2009, vol. 105, No. 084507, pp. 1-6.

Sun, Sam-Shajing, et al., Organic Photovoltaics: Mechanisms, Materials, and Devices, Boca Raton, Florida, CRC Press, Taylor & Francis Group, 2005.

Wobkenberg, et al., "Low-voltage organic transistors based on solution processed semiconductors and self-assembled monolayer gate dielectrics," Applied Physics Letters, 2008, vol. 93, No. 013303, pp. 1-3.

European Search Report dated Apr. 29, 2013 issued in connection with European Application No. 10 713 180.7.

First Office Action dated May 21, 2012 issued in connection with Chinese Application No. 200980127843.5, with English translation.

First Office Action dated Nov. 14, 2013 issued in connection with Chinese Application No. 201080025846.0.

Notice of Allowance dated Aug. 14, 2013 issued in connection with U.S. Appl. No. 13/003,923.

Office action dated Feb. 13, 2013 issued in connection with U.S. Appl. No. 13/003,923.

Office Action dated Nov. 20, 2013 issued in connection with Taiwan Invention Patent Application No. 098124092, with English translation.

Roe et al., The Synthesis of Dimethykaminoethyl Esters of Aromatic Phosphonic Acids, 1952, J. Org. Chem. Soc., vol. 18, pp. 362-366.

Schwartz et al., Advanced Surface Modification of Indium Tin Oxide for Improved Charge Injection in Organic Devices, 2005, J. Am. Chem. Soc., vol. 127, pp. 10058-10062.

Zaban et al., Molecular Adjustment of the Electronic Properties of Nanoporous Electrodes in Dye-Sensitized Solar Cells, 2005, J. Phys. Chem. B, vol. 109, pp. 189007-189013.

\* cited by examiner $t_{1/2}$ (Air plasma) = 97 Hrs
$t_{1/2}$ (FOPA, 7.9 mA/cm$^2$) > 150 Hrs
$t_{1/2}$ (FOPA, 6 mA/cm$^2$) > 325 Hrs q = 0-3

| Liquid | $\gamma_L^D$ (mN/m) | $\gamma_L^P$ (mN/m) | Drop Shape | $\theta_c$ (°) |
|---|---|---|---|---|
| Diiodomethane | 48.5 | 2.3 |  | 30.3 |
| Ethylene Glycol | 29.29 | 18.91 |  | 59.6 |
| Water | 21.8 | 51 |  | 100.5 |

ELECTRONIC DEVICES COMPRISING NOVEL PHOSPHONIC ACID SURFACE MODIFIERS

REFERENCE TO RELATED APPLICATIONS

This application claims priority to U.S. provisional application No. 61/166,877, filed Apr. 6, 2009, the whole content of which is herein incorporated by reference.

STATEMENT OF GOVERNMENT LICENSE RIGHTS

This invention was made with U.S. government support under grants from the STC Program of the National Science Foundation under Agreement Number DMR-020967. The U.S. Government has certain rights in the invention.

BACKGROUND

Organic electronic devices typically comprise organic electronic materials and an anode for hole injection or collection and a cathode for electron injection or collection. Modifying the work function of an electrode to move toward or away from the energy levels of the organic electronic material can improve device performance. Changing the composition of an electrode may result in undesirable effects such as more reactivity and less electrode stability. Modifying the surface of an electrode with, for example, air plasma treatment results in unstable work functions that change and approach the work function of the untreated electrode over time. Electrodes can be treated with molecules or polymers that may form thin layers (e.g., monolayers) to modify the work function of an electrode, but these thin layers may not provide ideal chemical resistivity. Increasing chemical resistivity of a surface by using fluoroalkyl compounds is known in the art to decrease adhesion (decrease wettability), and may adversely affect some parameters of device performance.

SUMMARY

One embodiment is a method, comprising: depositing a molecule on an electrode, wherein the electrode has a surface and the molecule has a binding group (e.g., an anchoring group) that binds to the surface, thereby providing a work function that is stable for at least 100 hours under ambient conditions (in air in the laboratory). In another embodiment, the work function of electrode with the bound molecule is the same as or similar to a work function that could be obtained by other surface modification means; but the work function of electrode with the bound molecule is more stable than a work function obtained by the other surface modification means. In some embodiments, the other surface modification means is air plasma treatment. In other embodiments, the electrode comprises an oxide and the molecule is a phosphonic acid (e.g., an alkyl phosphonic acid, a heteroalkyl phosphonic acid, an aryl phosphonic acid, or a heteroaryl phosphonic acid). Various other embodiments include organic electronic devices that comprise at least one electrode, the electrode having a surface and a molecule with a binding group bound to the surface, where the device is stable over a long period of time.

Another embodiment is a device comprising a) an electrode, the electrode having a surface; b) a molecule bound to the surface of the electrode through a binding group; and c) an organic electronic material in electrical contact with the electrode, wherein the molecule comprises at least one fluorinated aryl organic group. The fluorinated aryl groups provide superior chemical resistivity and long term stability while not adversely affecting the adhesion properties of the electrode.

Another embodiment is an organic electronic device comprising a) a transparent conductive metal oxide electrode having a surface and b) a fluorinated aryl phosphonic acid bound to the surface. In some embodiments, the fluorinated aryl phosphonic acid comprises a monolayer on the surface.

Another embodiment is a method, comprising: a) depositing a molecule on an electrode having a surface, the molecule comprising a binding and a fluorinated aryl group, whereby the binding group binds the surface and b) depositing an organic electronic material in proximity to the electrode so that the electrode and the organic electronic material are in electrical contact. The molecule may further comprise a linker group between the binding group and the fluorinated aryl group.

In some embodiments, the invention relates to a composition of matter comprising a molecule having the structure:

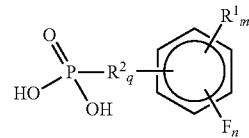

wherein: independently at each occurrence, $R^1$ is a halogen, a alkyl group, a heteroalkyl group, an aryl group, or a heteroaryl group; $R^2$ comprises from 3 to 30-$CH_2$— groups, n=0-5, m=0-5, q=1-3, and $R^2$ comprises at least one ether linkage.

DETAILED DESCRIPTION

Figure 1:
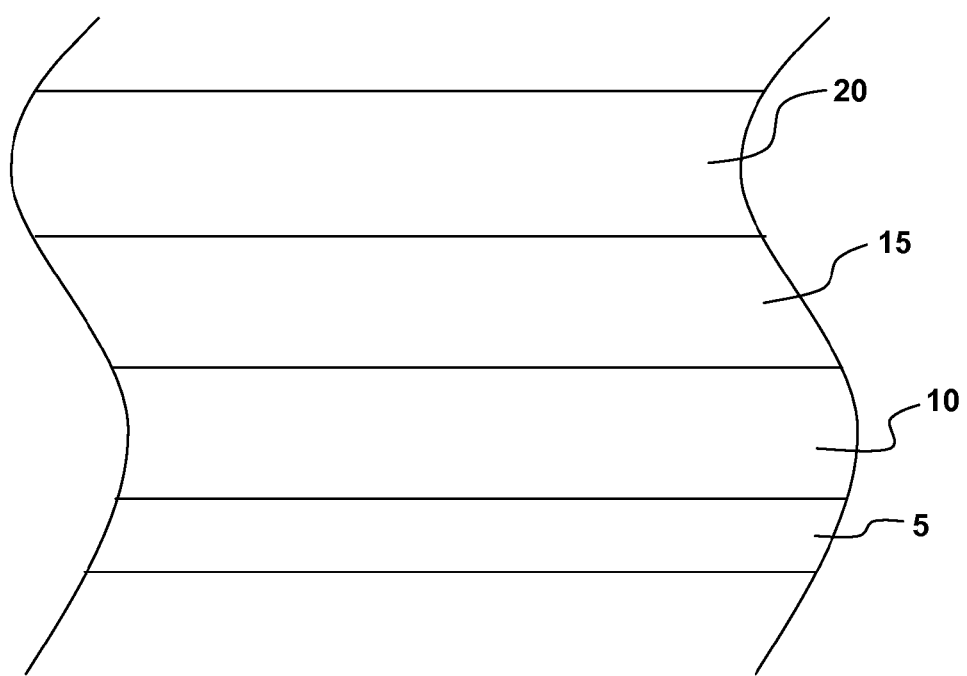
FIG. 1 illustrates a cross-section of part of an organic electronic device.

Various embodiments control the interface between organic electronic materials and a metal oxide electrode (e.g., controlling electronic properties, surface energy, wettability, adhesion properties, mechanical properties, chemical properties, or any combination thereof). One embodiment is a method, comprising: depositing a molecule on an electrode, wherein the electrode has a surface and the molecule has a binding group that binds to the surface, thereby providing a work function that is stable for at least 100 hours. Generally, "stable" refers to stability under ambient conditions or stability under inert operating conditions. In, many embodiments, the work function that is stable is different from the work function of the electrode before depositing the molecule. In another embodiment, the work function of electrode with the bound molecule is the same as or similar to a work function that could be obtained by other surface modification means (e.g., air plasma treatment); but the work function of an electrode with the bound molecule is more stable than a work function obtained by other surface modification means. In other embodiments, the work function of the electrode with the bound molecule maintains its measured work function within ±0.03 eV for more than 24 hours, whereas a work function obtained with other surface treatments decays rapidly to the value of the electrode before the other surface treatments. Typically, the molecule comprises a monolayer on the surface of the electrode. The binding group may be, for example, any of those known in the art such as, for example, a silane, a carboxylic acid, a sulfonic acid, a boronic acid, or a phosphonic acid. The molecule may comprise, for example, a binding group (also may be referred to as an anchoring group), a linker group, and substituent group. The binding group (e.g., —P(O)OH$_2$) is bonded to the linker group (e.g., —CH$_2$—) and the substituent group (e.g., —C$_6$F$_5$) is bound to the linker group. The binding group may be covalently or noncovalently bound to the surface. In many embodiments, the electrode comprises an oxide (e.g., indium tin oxide, indium zinc oxide, zinc oxide, gallium aluminum zinc oxide, antinomy tin oxide, fluorine tin oxide, cadmium oxide, or cadmium stannate, etc). In one embodiment, the work function is 4.5-5.6 eV. In other embodiments, the electrode comprises an oxide and the molecule is a phosphonic acid (e.g., an alkyl phosphonic acid, a heteroalkyl phosphonic acid, an aryl phosphonic acid, or a hetereoaryl phosphonic acid). The binding of phosphonic acids to oxide surfaces is known in the art, for example see S. H. Lee, et al., *J. Kor. Phys. Soc.* 49(5), 2034-2039 (2006) and S. Koh, et al., Langmuir, 22, 6249-6255 (2006). A wide variety of alkyl, heteroalkyl, aryl, or a hetereoaryl phosphonic acids with varying substituents may be prepared by methods known in the art, including, for example, by Michaelis-Arbuzov reaction of fluorinated aryl halides with trialkyl phosphite followed by hydrolysis (see Bhattacharya, A. K.; Thyagarajan, G. *Chem. Rev.* 1981, 81, 415-430), by photointiated Arbuzov reactions, metal catalyzed phosphorylation of aryl bromides (see Goossen, L. J., et al., *Synlett* 2005, (3), 445-448), and by hydrophosphorylation of alkenes (see Han, L.-B., et al., *J. Am. Chem. Soc.* 2000, 122, 5407-5408). The phosphonic acid may also contain an organometallic group such as ferrocene (e.g., *Inorg. Chim. Acta.* 2001, 322(1-2) 106-112). The organometallic group may be electroactive. In another embodiment, the method further comprises: b) depositing an organic electronic material in proximity to the modified electrode so that the electrode and the organic electronic material are in electrical contact. In other embodiments of the method, the electrode is an anode and the method further comprises: c) depositing a hole transport layer; d) depositing an electron transport layer; and e) depositing a cathode. For examples of organic electronic materials, methods, and devices, see: "Organic Electronics: Materials, Manufacturing and Applications" H. Klauk ed., Wiley-VCH, 2006; "Handbook of Organic Electronics and Photonics" H. S, Nalwa ed., American Scientific Publishers, 2006; "Organic Light Emitting Devices: Synthesis, Properties and Applications" K. Mullen ed., Wiley-VCH, 2006; "Organic Photovoltaics: Mechanisms, Materials, and Devices" S.-S. Sun and N. S. Sariciftci ed., CRC, 2005; and "Organic Field-Effect Transistors" Z. Bao and J. Locklin ed., CRC, 2007. "Electrical contact," when used herein regarding the electrode and the organic electronic material, means that electrical charges may flow between the electrode and the organic electronic material. The electrode and the organic electronic material may or may not be in physical contact. Electrons may flow to the electrode from the organic electronic material (e.g., hole injection) or electrons may flow from the electrode to the organic electronic material (e.g., electron injection). The organic electronic material may comprise any one of those known in the art, for example, a conducting polymer, a semi-conducting polymer, a hole transport polymer, an electron transport polymer, an emissive polymer, a solar absorbing polymer (e.g., an active layer in an organic photovoltaic), or a molecule (e.g., TPD, carbazole, pentacene, luminescent organometallics, etc.). The organic electronic material may also have, for example, a blend of two or more of hole transporters, electron transporters, emitters, solar absorbers, etc. as a guests in a host, covalently linked to a polymer, part of a polymer main chain, or any combination thereof.

Various embodiments include organic electronic devices that comprise at least one electrode, the electrode having a surface and a molecule with a binding group bound to the surface, where the device is stable over a long period of time. In one embodiment, the organic electronic device is more stable than if the electrode did not have the molecule bound to the surface. Organic electronic devices may include, for example, organic light emitting diodes, organic field effect transistors, organic photovoltaics, etc. In other embodiments, the organic electronic device with a bound molecule on the electrode has an efficiency that is the same as or similar to the efficiency of a device comprising an electrode having had a different surface treatment (e.g., air plasma treatment); but the half life ($t_{1/2}$) of the device with the bound molecule on the electrode is at least 50% greater. Typically, the molecule comprises a monolayer on the surface of the electrode. In one embodiment, referring to FIG. 1, the electrode is an anode 5 and the device further comprises: b) a hole transport layer 10 overlying the electrode. In another embodiment, the device further comprises: c) an electron transport layer 15 overlying the hole transport material and d) a cathode 20 overlying the electron transport material. Other devices layers, including for example emissive layers, may be in between any of the other devices layers. In other embodiment, the molecule, the electrode, the binding groups, and the organic electronic material may be as described above.

In one embodiment a device comprises a) an electrode, the electrode having a surface; b) a molecule bound to the surface of the electrode through a binding group; and c) an organic electronic material in electrical contact with the electrode, wherein the molecule comprises at least one fluorinated aryl group. There molecule may further comprise a linker group (e.g., —$CH_2$—, —$CH_2CH_2$—, —$CH_2CF_2$—, etc) between the binding group and the fluorinated aryl group. In some embodiments, the electrode comprises a transparent conductive metal oxide. Examples of transparent conductive metal oxides include indium tin oxide, indium zinc oxide, zinc oxide, gallium aluminum zinc oxide, antinomy tin oxide, fluorine tin oxide, cadmium oxide, or cadmium stannate, etc). In other embodiments, the electrode comprises a carbon nanotubes or graphene that is functionalized to react with the binding group (e.g., so that a phosphonic acid binds to the carbon nanotube or grapheme by through the functionalized group). In many embodiments, the molecule comprises a monolayer on the surface. The binding group of the molecule may comprise, for example, a silane, a carboxylic acid, a sulfonic acid, a boronic acid, or a phosphonic acid. In some embodiments, the fluorinated aryl group comprises a phenyl group, a naphthalene group, or a biphenyl group and the number of fluorines is from 1 to 10. In another embodiment, the binding group is a phosphonic acid and the conductive transparent oxide is indium tin oxide. The molecule comprising the fluorinated aryl group may modify the work function of the electrode and provide a work function that is comparatively stable while maintaining good wettability of the electrode surface (allows adhesion).

Another embodiment is an organic electronic device comprising a) a transparent conductive metal oxide electrode having a surface and b) a fluorinated aryl phosphonic acid bound to the surface. In some embodiments, the fluorinated aryl phosphonic acid comprises a monolayer on the surface. A wide variety of fluorinated aryl phosphonic acids may be prepared by methods known in the art such as those described above. In other embodiments, for example when the electrode is indium tin oxide (ITO), the contact angle formed by a drop of water on the surface of the fluorinated aryl phosphonic acid bound ITO is between 60° and 80°. In another embodiment, the surface energy is from 30 $mJ/m^2$ to 50 $mJ/m^2$. In other embodiments, the surface energy is from 35 $mJ/m^2$ to 45 $mJ/m^2$. In other embodiments, the polar component of the surface energy is from 0 $mJ/m^2$ to about 15 $mJ/m^2$. In some embodiments, the fluorinated aryl group comprises from 1 to 11 fluorines. In one embodiment, the fluorinated phosphonic acid has the structure

Figure 2:
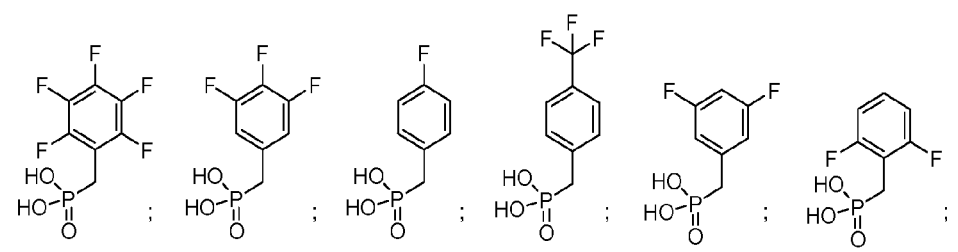
FIG. 2 shows some fluorinated aryl phosphonic acids.
Figure 2:
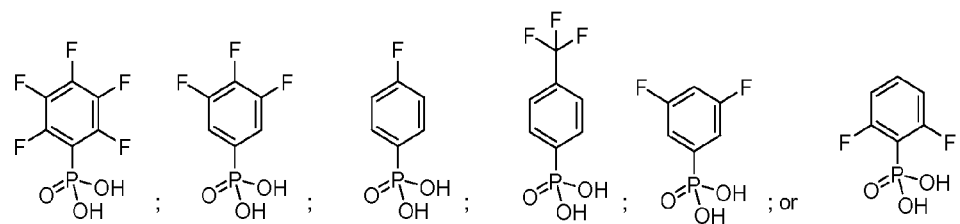

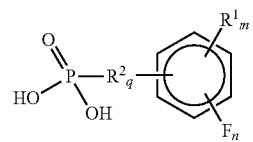

wherein, independently at each occurrence: $R^1$ is a halogen, alkyl, heteroalkyl, or a fluorinated alkyl group; $R^2$ is methylene, fluorinated methylene, alkene, or alkyne; n=0-5; m=0-3; and q=0-3, provided that at least one fluorine is present. Other embodiments include phosphonic acids comprising fluorinated aryl groups. In other embodiments, the transparent conductive metal oxide is an anode and the organic electronic device further comprises: c) a hole transport layer overlying the fluorinated aryl phosphonic acid; d) an electron transport layer overlying the hole transport layer; and e) a cathode overlying the electron transport layer. Materials used for the hole transport layer, the electron transport layer, and the cathode may be selected from polymers, small molecules, composites, metals, or any combination thereof as is known in the art. In some embodiments, the work function of the anode is between 4.4 eV and 5.6 eV. In other embodiments, the fluorinated phosphonic acid corresponds to one of the structures illustrated in FIG. 2.

Another embodiment is a method, comprising: a) depositing a molecule on an electrode, the electrode having a surface and the molecule comprising a binding group and a fluorinated aryl group, whereby the binding group binds the surface and b) depositing an organic electronic material in proximity to the electrode so that the electrode and the organic electronic material are in electrical contact. Depositing the molecule and depositing the organic electronic material may independently include techniques such as, for example, spin coating, dip coating, drop casting, evaporation, crosslinking, vacuum deposition, or any combination thereof in a single step or in discrete steps. In many embodiments, the molecule comprises a monolayer on the surface. In other embodiments, the electrode comprises a transparent conductive metal oxide. The conductive transparent conductive metal oxide and the binding may be as described above. In other embodiments, for example when the electrode is indium tin oxide (ITO), the contact angle of the fluorinated aryl phosphonic acid bound ITO is between 60° and 80°. In another embodiment, the surface energy is from 30 $mJ/m^2$ to 50 $mJ/m^2$. In other embodiments, the surface energy is from 35 $mJ/m^2$ to 45 $mJ/m^2$. In some embodiments, the fluorinated aryl group comprises a phenyl group, a naphthalene group, or a biphenyl group and the number of fluorines is from 1 to 10. In some embodiments, binding group is a phosphonic acid and the conductive transparent oxide is indium tin oxide. In another embodiment, the fluorinated aryl group may comprise from 1 to 11 fluorines. In other embodiments, the molecule is a fluorinated phosphonic acid that has the structure

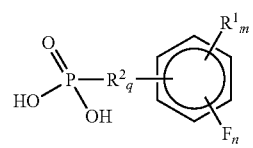

wherein, independently at each occurrence: $R^1$ is a halogen, alkyl, heteroalkyl, or fluorinated alkyl group; $R^2$ is methylene, fluorinated methylene, alkene, or alkyne; n=0-5; m=0-3;

and q=0-3, provided that at least one fluorine is present. In another embodiment, the work function of the electrode is between 4.4 eV and 5.6 eV. In other embodiments, the transparent conductive metal oxide is an anode and the method further comprises: c) depositing an hole transport layer; d) depositing an electron transport layer; and e) depositing a cathode. In another embodiment, fluorinated phosphonic acid has any one of the structures in FIG. 2.

Another embodiment is a phosphonic acid having the structure

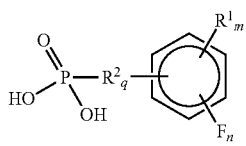

where, $R^2$ comprises 3 to 30-$CH_2$— groups, n=0-5, m=0-5, and $R^1$ is as described above. In some such preferred embodiments, $R^2$ is bonded to the phenyl ring through an ether. $R^1$ may also be a functional group that can be reacted with other compounds or polymers or crosslinked. In such preferred embodiments, q can be an integer between 1-3.

In some such preferred embodiments, $R^2$ comprises at least one ether linkage. In related embodiments, $R^2$ comprises —$(CH_2)_x$—$O_y$—$(CH_2)_x$—$O_y$—$(CH_2)_z$— wherein, independently at each occurrence, x=1-12, y=0-1, and z=0-4. Other embodiments are devices and methods comprising the phosphonic acid. One embodiment is a transistor comprising the phosphonic acid.

In some preferred embodiments, the invention relates to a composition of matter comprising a molecule having the structure:

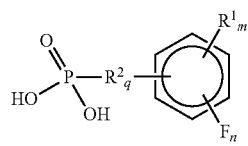

wherein: independently at each occurrence, $R^1$ is a halogen, a alkyl group, a heteroalkyl group, an aryl group, or a heteroaryl group; $R^2$ comprises from 3 to 30 —$CH_2$— groups, n=0-5, m=0-5, q=1-3, and $R^2$ comprises at least one ether linkage.

In the preferred compositions comprising $R^2$ ether linker groups, the composition can be an electrode having a surface, and optionally the phosphonic acid binding group of the molecule can be bound to the electrode surface. In such embodiments, when the phosphonic acid binding group binds to the electrode surface, one or both of the hydrogen atoms of the phosphonic acid group may be lost, and the oxygen atoms of the phosphonic acid group can optionally form covalent bonds to the surface.

In the preferred compositions comprising $R^2$ ether linker groups, $R^2$ can be bonded to the phenyl ring through an ether group, or $R^2$ can have the structure:

—$(CH_2)_x$—$O_y$—$(CH_2)_x$—$O_y$—$(CH_2)_z$— wherein, independently at each occurrence, x=1-12, y=0-1, and z=0-3. The $R^2$ ether linker group can also be bound to the optionally substituted phenyl ring via a benzylic carbon atom, as exemplified by the structures below:

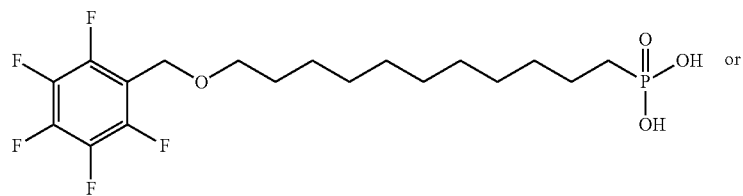

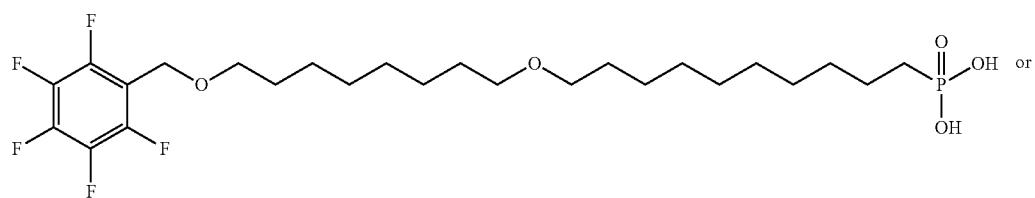

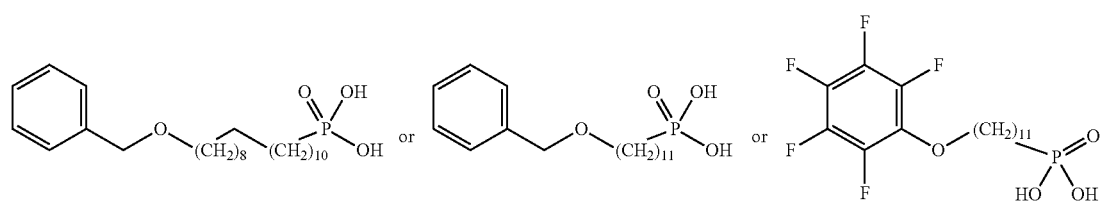

In such compositions, n the number of fluorine atoms, can be any integer from 0 to 5, i.e. 0, 1, 2, 3, 4, or 5. In many embodiments, at least one fluorine is optionally present on the phenyl ring. In many embodiments, 5 fluorine atoms are present on the phenyl ring.

The ether linked phosphonic acid compounds, or their compositions, may be incorporated into many devices, especially electronic devices that may comprise electrodes, such as for example field effect transistors having source, drain, and gate electrodes, and many such electrodes, especially gate electrodes, comprise metal oxide surfaces. In such embodiments, the phosphonic acid group of the ether linked phosphonic acid compounds can bind non-covalently or covalently to the surface of a metal oxide, and may optionally form a monolayer on the metal oxide surface of the electrode. If the phosphonic acid group of the ether linked phosphonic acid compounds bind to the metal oxide surface covalently, it is to be understood that one or both of the hydrogen atoms of the phosphonic acid groups may be removed during the binding process.

As evidenced in the Examples and Figures attached herewith, the binding of the ether linked phosphonic acid compounds to electrode surfaces can have an unexpectedly superior effect of forming a dielectric layer on the electrode surfaces, and/or very significantly improving the "wettability" of the electrode surface by organic molecules, such as organic semiconductors, significantly improving the manufacture, durability, properties, and/or performance of electronic devices comprising the modified electrodes.

Applicants inventions also comprise methods of modifying the surface energy of an electrode by depositing the ether linked phosphonic acid compounds or a composition comprising them on the surface of the electrode, and in such methods the ether linked phosphonic acid compounds can bind to the electrode, preferably forming a monolayer of the ether linked phosphonic acid compound on the electrode surface.

Another embodiment is a method of modifying the surface energy of an electrode so that some interaction property between the electrode and an organic electronic material (e.g., adhesion) is improved. In most embodiments, the surface energy of the electrode is modified by depositing a molecule that binds to the surface of the electrode (e.g., as described herein). The molecule may form a monolayer. In some embodiments, the work function is not significantly modified. In other embodiments, the work function is modified to increase or decrease the flow of electrons to or from the organic electronic material. One embodiment is a method, comprising: a) providing an electrode having a surface, a first work function, and a first surface energy; and b) depositing a molecule on the surface, thereby providing a modified electrode with a second work function and a second surface energy, wherein the molecule binds to the electrode through a binding group and the first surface energy and the second surface energy are different. In one embodiment, the second surface energy is different from the first surface energy so that adhesion of an organic electronic material to the modified electrode is better than the adhesion of the organic electronic material to the electrode, wherein electrons can flow between the organic electronic material and the electrode. In another embodiment, the second work function is different from the first work function so that electron flow between the organic electronic material and the electrode is improved. In other embodiments, the second surface energy is different from the first surface energy so that adhesion of an organic electronic material to the modified electrode is better than the adhesion of the organic electronic material to the electrode, wherein electrons can flow between the organic electronic material and the electrode and wherein the second work function is different from the first work function so that electron flow between the organic electronic material and the electrode is improved. In one embodiment, the electrode is a transparent conductive metal oxide and the second surface energy is from about 20 $mJ/m^2$ to about 50 $mJ/m^2$ and the work function is about 4.4 eV to about 5.6 eV. In some embodiments, the polar component of the surface energy is from 0 $mJ/m^2$ to about 15 $mJ/m^2$. In another embodiment, the molecule forms a monolayer on the surface. In another embodiment the transparent conductive metal oxide comprises indium tin oxide, indium zinc oxide, zinc oxide, gallium aluminum zinc oxide, antinomy tin oxide, fluorine tin oxide, cadmium oxide, or cadmium stannate the molecule is a phosphonic acid. In another embodiment, the molecule is an alkyl phosphonic acid, a heteroalkyl phosphonic acid, an aryl phosphonic acid, or a hetereoaryl phosphonic acid. In another embodiment, the first work function and the second work function are different and the second surface energy and the first surface energy are essentially the same.

Other embodiments include phosphonic acids, for example, as some of those shown in FIGS. 2, 9, 10, and 14 and Table 1. These phosphonic acids bind to the surface of metal oxides and/or comprise an organic electronic device as described above.

Figure 14:
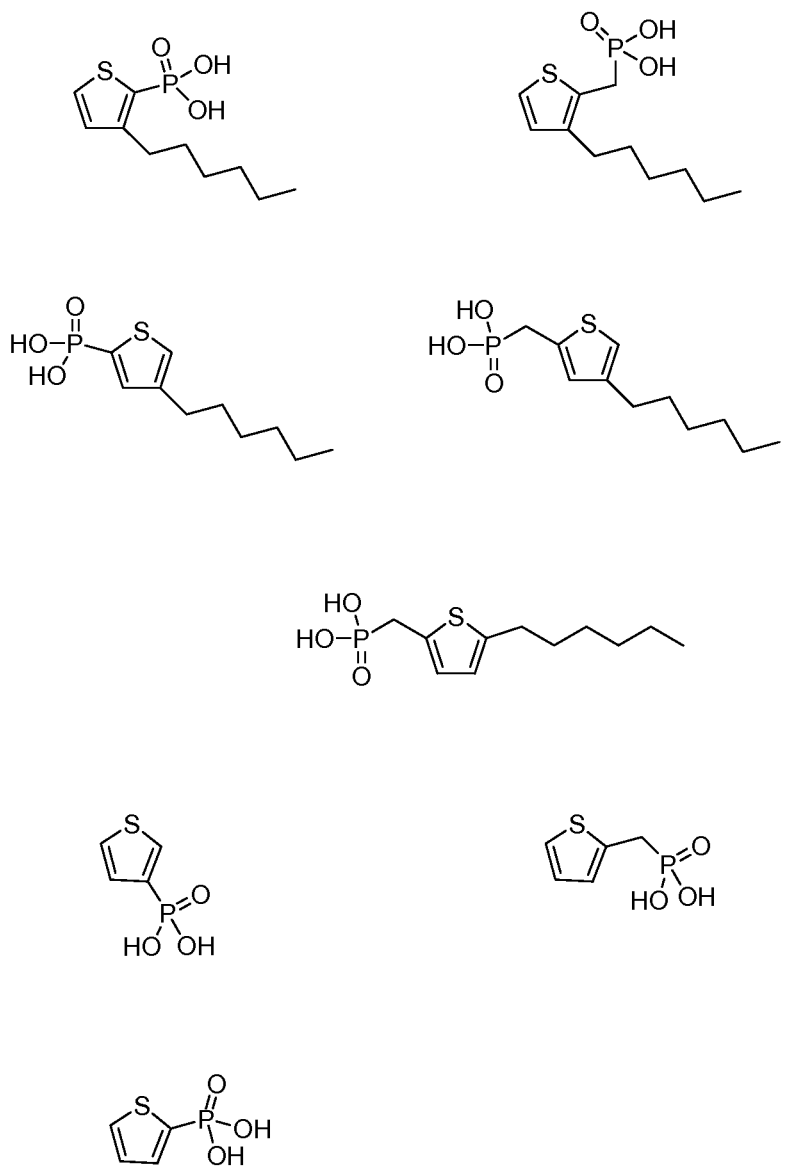
FIG. 14 shows thiophene containing phosphonic acids.

Other embodiments include thiophene containing phosphonic acids. Thiophene containing phosphonic acids bind to the surface of metal oxides and/or comprises an organic electronic device as described above. Examples of thiophene containing phosphonic acids are shown in FIG. 14. In one embodiment, a thiophene containing phosphonic acid improves compatibility and/or adhesion of the thiophene containing hole transport polymer to the surface of a metal oxide to which the thiophene containing phosphonic acid is bound.

Figure 15:
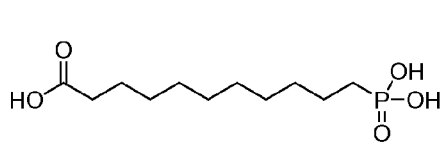
FIG. 15 shows some functional group containing phosphonic acids.
Figure 15:
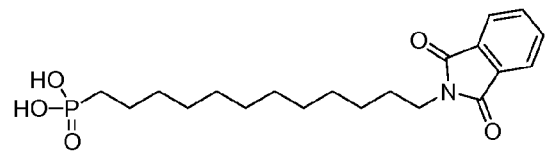
Figure 15:
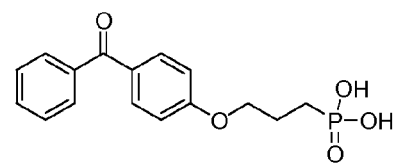
Figure 15:
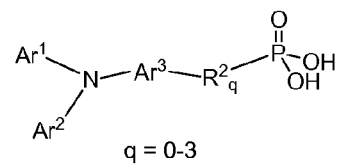
Figure 16:
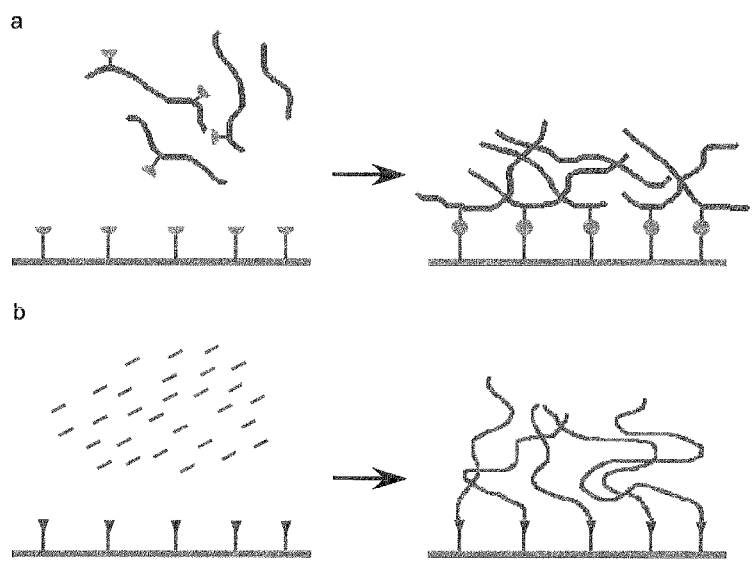
FIG. 16 shows methods of grafting polymers onto a surface comprising functional group containing phosphonic acids.

Other embodiments include a phosphonic acid comprising a functional group. A phosphonic acid comprising a functional group binds to the surface of metal oxides and/or comprises an organic electronic device as described above. The functional group may be reactive towards a wide variety of compounds including, for example, molecules, polymers, biopolymers, proteins, nucleic acids, etc. The functional groups may be, for example, electrophilic, nucleophilic, may generate radicals, may be photoreactive, or any combination thereof. The functional group may be, for example, a carboxylic acid, an acrylate, an amine, an aldehyde, a ketone, an alkene, alkyne, or any one of those known in the art. The functional groups may also be protected as, for example, esters, carbamates, phthalimides, and the like. Some examples of phosphonic acids containing functional groups are shown in FIG. 15. Other embodiments include molecules and/or polymers for reacting with the functional groups. When the phosphonic acid is bound to the surface of a metal oxide, the functional group may be reacted with a second molecule and/or polymer to bind (e.g., covalently bond) the second molecule and/or polymer to the surface. In one embodiment, a benzophenone functional group reacts with a —C—H bond in a polymer. Other embodiments include methods of reacting the functional groups with molecules and/or polymers, articles made by the methods, and organic electronic devices made by the methods. In another embodiment, the functional group is used to react with a monomer and grow polymers from the surface. An illustration of reacting the functional group with a polymer (e.g., attaching the polymer to the surface via a functional group on the surface) is shown in FIG. 16*a* and an illustration of polymerizing from the functional groups is shown in FIG. 16*b*. Other embodiments include methods of binding a molecule and/or polymer to the surface of a metal oxide comprising reacting a phosphonic acid comprising a functional group with the molecule and/or polymer, wherein the phosphonic acid is bound to the surface of the metal oxide and the functional group reacts with the molecule and/or polymer. Other embodiments include organic electronic devices or sensors (e.g., biosensors) made by processes comprising reacting a functional group containing phosphonic acid with a molecule and/or polymer, wherein the phosphonic acid is bound to the surface of a metal oxide and the functional group reacts with the molecule and/or polymer. Other embodiments include methods of growing a polymer from the surface of a metal oxide comprising reacting a functional group containing a phosphonic acid with a monomer of the polymer, wherein the phosphonic acid is bound to the surface of the metal oxide. Other embodiments include organic electronic devices or sensors (e.g., biosensors) made by a process comprising reacting a molecule, the molecule having a functional group and a phosphonic acid, with a monomer of the polymer, wherein the phosphonic acid is bound to the surface of the metal oxide. The polymerization process may include, for example, a ring opening metathesis polymerization (ROMP), a radical polymerization, an anionic polymerization, a cationic polymerization, a condensation polymerization.

Another embodiment is a phosphonic acid comprising a triarylamine and organic electronic devices comprising the triarylamine-phosphonic acid. The triarylamine may comprise the structure:

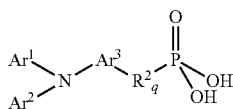

where Ar is independently at each occurrence an aryl group, $R^2$ is methylene, fluorinated methylene, alkene, or alkyne, and q=0-3. Each Ar group may be independently substituted with aryl group, hetereoaryl group, alkyl group, heteroalkyl group, or halogen. The $Ar^3$ group may be ortho, meta, or para substituted with respect to N and $R^2$ when $Ar^3$ is a benzene ring. In another embodiment, one or more of $Ar^1$, $Ar^2$, and/or $Ar^3$ are substituted with —$NAr^4_2$, wherein $Ar^4$ is independently at each occurrence an aryl or a hetereoaryl group. In some embodiments, $Ar^1$ is substituted with —$NAr^4_2$ and $Ar^1$ is a benzene ring, a biphenyl, or a naphthyl. In some embodiments, neighboring Ar groups may be linked (e.g., with a single bond, an ethylene linkage, a heteroalkyl bridge, multiple bond/s, or atoms in an aryl or hetereoaryl ring) to form one or more rings (e.g., if $Ar^1$ and $Ar^2$ are joined together by a single bond to form a carbazole).

Other embodiments include polymers comprising phosphonic acids and organic electronic devices or sensors comprising a polymer comprising phosphonic acids bound to the surface of a metal oxide. The polymers may be, for example, homopolymers or copolymers. Copolymers may comprise monomers or different compositions, monomers that are isomers, monomers that are stereoisomers, or any combination thereof. The copolymers may include, for example, other functional groups (such as described above), compatibilizing groups (e.g., PEG), or anti-fouling groups (e.g., fluorinated groups) or any combination thereof. Other embodiments include methods of binding polymers comprising phosphonic acids to the surface of a metal oxide and article made by the method.

EXAMPLES

The following examples are illustrative and do not limit the claims.

Methods used to characterize the electrode surface:

X-ray photoelectron spectroscopy (XPS) and UV-photoelectron spectroscopy (UPS): XPS with a monochromatic Al(Kα) source (300 W) and UPS (He I excitation source) were performed as stated elsewhere [Alloway, D. M.; Hofmann, M.; Smith, D. L.; Gruhn, N. E.; Graham, A. L.; Colorado, R.; Wysocki, V. H.; Lee, T. R.; Lee, P. A.; Armstrong, N. R. *J. Phys. Chem. B* 2003, 107, 11690-11699] using a Kratos Axis-Ultra spectrometer, with the Fermi energy (EF) calibrated frequently using an atomically clean gold sample. All ITO samples were in electronic equilibrium with the spectrometer, i.e. that the Fermi energy for each sample was known. All XPS spectra were acquired before UPS data acquisition. All characterizations were performed at normal takeoff angle (0°) unless otherwise noted.

Contact angle: These measurements were conducted on a KRÜSS prop Shape Analysis System DSA 10Mk2, using water and hexadecane as probe liquids (0.5 µL). Several drops (typically 6 repetitions) were quickly placed on the surface, the needle pulled back, and the drop shape captured immediately with the camera. Images were analyzed with the prop Shape Analysis software to determine the contact angle by the method most suitable for each given drop, usually circle fitting, and averaging the results. The contact angle data was used to calculate the components of the surface energy by the harmonic means method.

Preparation of ITO with Bound Molecule

ITO coated glass substrates (20Ω/□, Colorado Concept Coatings, L.L.C.) were first cleaned in an ultrasonic bath using a dilute solution of Triton-X (Aldrich) in DI water for 20 minutes. The ITO substrates were then thoroughly rinsed in DI water and a final ultrasonication for 20 min. in DI water. Further organic cleaning was done in the ultrasonic bath using acetone and ethanol, 20 minutes each. After every step during the cleaning, the samples were blown using a nitrogen gun to blow off remaining solvent from the ITO surface.

Washed ITO substrates were then dried in a vacuum drying oven at 70° C. under a pressure of ($1 \times 10^{-2}$ Torr) for overnight.

SiOx Barrier Layer Formation

For the device structure, a passivation layer of 300 nm SiOx was deposited some parts of the substrate by e-beam on ITO with a shadow mask to define areas in which electrical contact could be physically made to the top cathode without creating electrical shorts between the anode and the cathode for various devices. The deposition of SiOx was done at the rate of 4 Å/s and, at pressure below $1 \times 10^{-6}$.

Monolayer Formation:

The organophosphonic acid (1 mM in $CHCl_3$:$C_2H_5OH$::2:1) was stirred overnight at room temperature; the resulting solution was filtered through 0.2 micrometer PTFE; ITO substrates as prepared above were submerged in the phosphonic acid solution at room temperature and the solution was allowed to evaporate until 1 hr Substrates were then annealed on the hot plate at 120° C. for 1 hr. The temperature was then brought down to room temperature before any organic layer deposition for devices or work function measurements. All the monolayer formation steps and solution processing were performed in a nitrogen filled glove box (GB) having $H_2O$ level below 1 ppm and air level below 20 ppm.

Electrode Work Function Stability and Device Stability

Figure 3:
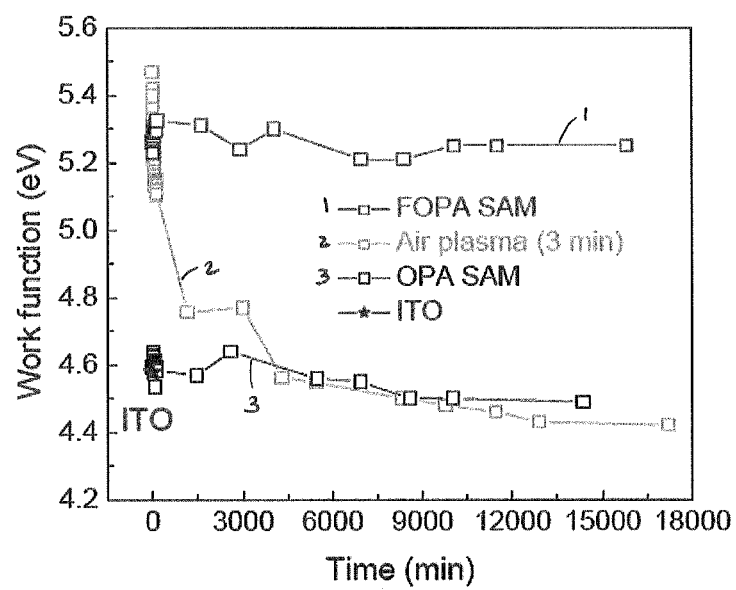
FIG. 3 shows stability of the work function of ITO with surface-bound phosphonic acids compared to ITO treated with air plasma.
Figure 4:
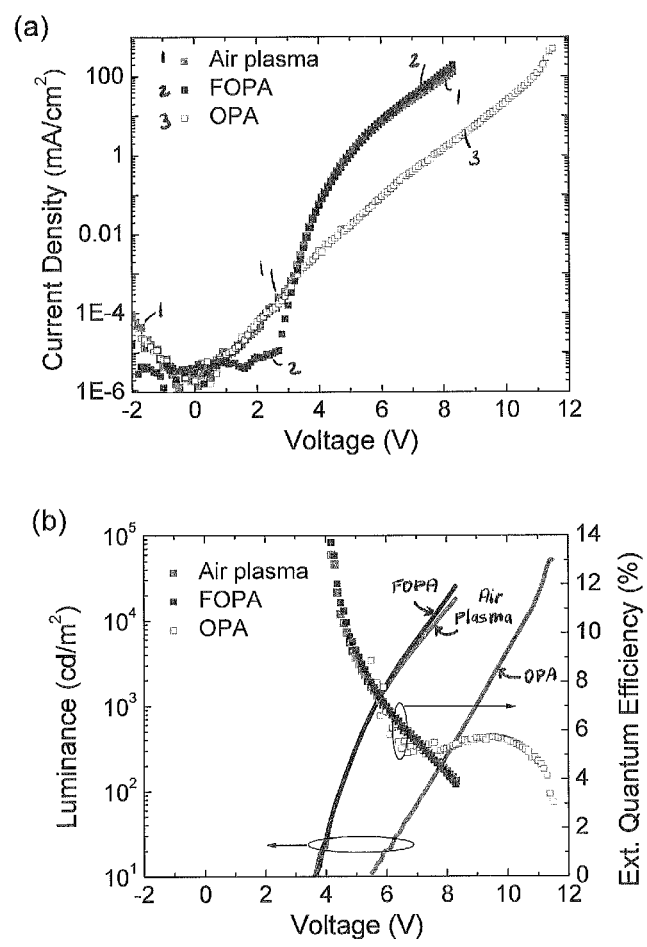
FIG. 4 shows (a) the current-voltage (I-V), and (b) the luminance/external quantum efficiency (EQE) graphs for devices with ITO with surface-bound phosphonic acids compared to devices with ITO treated with air plasma.
Figure 5:
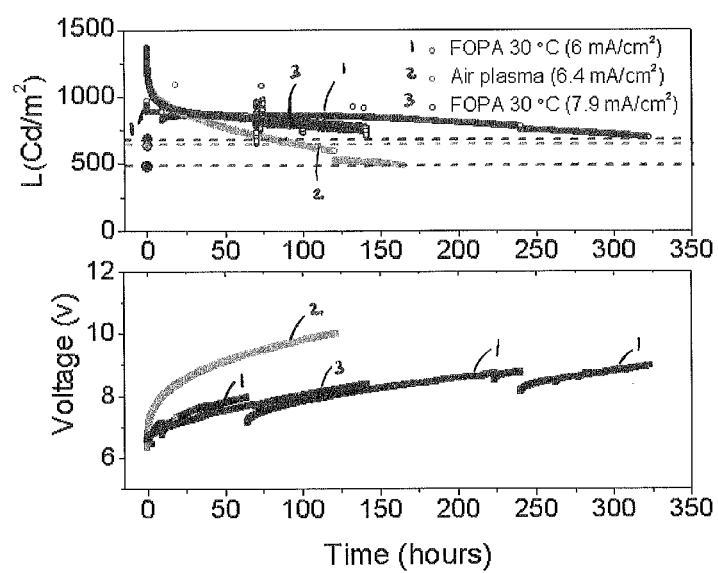
FIG. 5 shows the stability of devices with ITO with surface-bound phosphonic acids compared to devices with ITO treated with air plasma.

FIG. 3 shows examples of the much improved stability of the work functions of both ITO with bound molecules of octyl phosphonic acid (OPA) and ITO with bound molecules of 3,3,4,4,5,5,6,6,7,7,8,8,8-tridecylfluorooctyl phosphonic acid (FOPA) compared to ITO treated with air plasma. The lifetime of devices fabricated with FOPA bound to the surface of ITO (FIG. 5) showed increased stability.

Fluorinated Aryl Phosphonic Acids

Examples of other molecules that were bound to the surface of Indium Tin Oxide (ITO) are shown in Table 1.

TABLE 1

| Molecule | Synthesis |
| --- | --- |
| F5BPA | Rice, Bobbie L.; Guo, Cai Yun; Kirchmeier, Robert L. Inorganic Chemistry (1991), 30(24), 4635-8. |
| F3BPA | Synthesis described below |
| F1BPA | Montoneri, E.; Savarino, P.; Viscardi, G.; Gallazzi, M. C. Organosulfur phosphorus acid compounds. Part 4. Fluorobenzyl-phosphonosulfonic acids. Phosphorus, Sulfur and Silicon and the Related Elements (1994), 86(1-4), 145-55. |
| CF3BPA | Schwender, Charles; Demarest, Keith; Wustrow, David. Preparation of trifluoromethylbenzylphosphonates useful treating osteoporosis. Eur. Pat. Appl. (1993), 12 pp. CODEN: EPXXDW EP 524023 A1 19930120 CAN 118: 234243 AN 1993: 234243. |//

TABLE 1-continued

| Molecule | Synthesis |
| --- | --- |
| F3PPA | Synthesis described below |
| CF3PPA | ChemPacific Product List #60139, CAS #1869-27-8 |

Synthesis of Diethyl 3,4,5-trifluorobenzylphosphonate 3,4,5-trifluorobenzyl iodide (5.075 g, 22.55 mmol) was combined with triethylphosphite (11.6 mL, 67.7 mmol) and the mixture heated and stirred at 135° C. overnight. The mixture was put under hi-vacuum and heated to 70° C. for 12 hours. The final product was a clear oil (6.10 g, 96% yield). $^1$H NMR (400.14 MHz, CDCl$_3$) δ 6.93 (m, 2H), 4.07 (quint, J=7.10 Hz, 4H), 3.06 (d, J=21.7 Hz, 2H), 1.28 (t, J=7.05 Hz, 6H). $^{13}$C{$^1$H} NMR (100.62 MHz, CDCl$_3$) δ 150.8 (dddd, J=249.7, 9.8, 3.8, 3.8 Hz, 2C), 138.74 (dtd, J=250.6, 15.2, 3.9 Hz), 128.2-127.9 (m), 113.9-113.6 (m, 2C), 62.30 (d, J=6.74 Hz, 2C), 32.93 (d, J=139.8 Hz), 16.20 (d, J=6.01 Hz, 2C). $^{31}$P{$^1$H} NMR (202.45 MHz, CDCl$_3$): δ 24.96. Analysis calculated (found) %: C 46.82 (46.72), H 5.00 (4.96). MS (FAB, m/z): 269 (M$^+$, 100%). Exact mass calculated (found) for [M+H]$^+$, m/z): 269.05544 (269.05616).

Synthesis 3,4,5-trifluorobenzylphosphonic acid (F3BPA)

Diethyl 3,4,5-trifluorobenzylphosphonate (2.80 g, 9.92 mmol) was dissolved in dry dichloromethane (30 mL). Bromotrimethylsilane (4.1 mL, 31.7 mmol) was added via syringe. The reaction was capped with a greased glass stopper and allowed to stir for 6 hours. The volatiles were removed under reduced pressure to yield a yellow oil. This was dissolved in 10:1 methanol:water (20 mL) and allowed to stir overnight. After removing the solvents, recrystallization in acetonitrile yielded large white needles (2.00 g, 89% yield). $^1$H NMR (400.14 MHz, DMSO) δ 7.16 (m, 2H), 2.99 (d, J=21.4 Hz, 2H). $^{13}$C {$^1$H} NMR (100.62 MHz, DMSO) δ 149.9 (dddd, J=246, 9.6, 3.6, 3.6 Hz, 2C), 137.5 (dtd, J=247, 15.4, 3.7), 132.1-131.8 (m), 114.4-114.1 (m, 2C), 34.42 (d, J=132 Hz). $^{31}$P {$^1$H} NMR (161.97 MHz, DMSO): δ 20.54. Analysis calculated (found) %: C 37.19 (37.17), H 2.67

(2.63). MS (FAB, m/z): 227 (M+, 100%). Exact mass calculated (found) for [M+H]+, m/z): 227.00849 (227.00670).

Synthesis of diethyl 3,4,5-trifluorophenylphosphonate

Trifluorobromobenzene (1.70 mL, 14.2 mmol), diethyl phosphite (2.20 mL, 17.1 mmol), N,N-dicyclohexylmethylamine (4.60 mL, 21.3 mmol) and ethanol (50 mL) were all combined in a nitrogen purged round bottom flask. After stirring for 5 minutes, triphenylphosphine (223 mg, 0.85 mmol) and palladium acetate (64 mg, 0.28 mmol) were added to the flask as one. The solution was heated to 76° C. and allowed to stir overnight. The solution started as a translucent brown color but was clearer by morning. Upon cooling, a silica plug (starting with hexanes as eluent, and increasing the polarity with ethyl acetate as needed) was run and a UV-active spot ($R_f$=0.35 in 1:1 hexanes:ethyl acetate) was isolated. The final product is a clear oil (3.477 g, 91% yield). $^1$H NMR (400.14 MHz, CDCl$_3$) δ 7.44 (dt, J=14.4, 6.50 Hz 2H), 4.19-4.07 (m, 4H), 1.34 (t, J=7.07 Hz, 6H). $^{13}$C {$^1$H} NMR (100.62 MHz, CDCl$_3$) δ 151.1 (dddd, J=254.7, 25.4, 10.1, 2.9 Hz, 2C), 142.5 (dtd, J=258.6, 15.1, 3.3 Hz), 125.0 (dtd, J=194.5, 5.8, 5.2 Hz), 116.3-116 (m, 2C), 62.72 (d, J=5.63 Hz, 2C), 16.16 (d, J=6.34 Hz, 2C). $^{31}$P {$^1$H} NMR (161.97 MHz, CDCl$_3$): δ 14.94. Analysis calculated (found) %: C 44.79 (44.51), H 4.51(4.65). MS (FAB, m/z): 283 (M+, 100%). Exact mass calculated (found) for [M+H]+, m/z): 283.07109 (283.07135).

Synthesis of 3,4,5-trifluorophenylphosphonic acid (F3PPA)

12 M HCl (12 mL, excess) was added to diethyl 3,4,5-trifluorophenylphosphonate (320 mg) in a round bottom flask. The reaction mixture was refluxed for 12 hours. A brown oil was obtained after cooling and removal of the solvent. $^1$H NMR showed the presence of unreacted starting material. 12 mL of 8 M HCl was added and the reaction mixture refluxed again for several days. The mixture was allowed to cool and stand for several weeks. An off-white solid was obtained after removal of the solvent (190 mg, 76% yield). $^1$H NMR (400.14 MHz, DMSO) δ 7.49-7.42 (m, 2H). $^{13}$C {$^1$H} NMR (100.62 MHz, DMSO) δ 150.1 (dddd, J=251.0, 23.7, 7.3, 2.6 Hz, 2C), 140.5 (dtd, J=253.1, 15.3, 2.6 Hz), 131.8 (dm, J=178.4 Hz), 115.3-114.9 (m, 2C). $^{31}$P {$^1$H} NMR (161.97 MHz, DMSO): δ 9.22. Analysis calculated (found) %: C 33.98 (33.94), H 1.90 (1.80). MS (FAB, m/z): 213 (M+, 100%). Exact mass calculated (found) for [M+H]+, m/z): 212.99284 (212.99418).

Synthesis of diethyl 3,5-difluorobenzylphosphonate 3,5-difluorobenzyl bromide (3.0 mL, 23.2 mmol) was combined with triethylphosphite (9.1 mL, 53.3 mmol) and the mixture heated and stirred at 135° C. overnight. The mixture was put under hi-vacuum and heated to 70° C. for 12 hours. The final product was a clear oil (5.78 g, 94% yield). $^1$H NMR (400.14 MHz, CDCl$_3$) δ 6.83 (m, 2H), 6.71 (dt, J=9.00, 2.28 Hz), 4.06 (m, 4H), 3.12 (d, J=21.94 Hz, 2H), 1.28 (t, J=7.09 Hz, 6H). $^{31}$P {$^1$H} NMR (161.97 MHz, CDCl$_3$): δ 25.22.

Synthesis of 3,5-difluorobenzylphosphonic acid

Diethyl 3,5-difluorobenzylphosphonate (3.00 g, 11.4 mmol) was dissolved in dry dichloromethane (25 mL). Bromotrimethylsilane (4.9 mL, 37 mmol) was added via syringe. The reaction was capped with a greased glass stopper and allowed to stir for 6 hours. The volatiles were removed under reduced pressure to yield a yellow oil. This was dissolved in 8:1 methanol:water (25 mL) and allowed to stir overnight. After removing the solvents, recrystallization in acetonitrile yielded a white crystalline solid (1.98 g, 91% yield). $^1$H NMR (400.14 MHz, DMSO) δ 7.05 (dt, J=9.49, 2.09 Hz), 6.95 (d, J=8.54 Hz, 2H), 3.02 (d, J=21.57 Hz, 2H). $^{31}$P {$^1$H} NMR (161.97 MHz, DMSO): δ 20.63. Analysis calculated (found) %: C 40.40(40.67), H 3.39 (3.39).

Synthesis of diethyl 2,6-difluorobenzylphosphonate 2,6-difluorobenzyl bromide (3.0 g, 14.5 mmol) was combined with triethylphosphite (6.2 mL, 36.2 mmol) and the mixture heated and stirred at 135° C. overnight. The mixture was put under hi-vacuum and heated to 80° C. for 10 hours. The final product was a slightly yellow-tinted oil (3.30 g, 86% yield). $^1$H NMR (400.14 MHz, DMSO) δ 7.36 (m), 7.10 (m, 2H), 3.96 (m, 4H), 3.20 (d, J=21.08 Hz, 2H), 1.16 (t, J=7.05 Hz, 6H). $^{13}$C {$^1$H} NMR (100.62 MHz, CDCl$_3$) δ 161.0 (ddd, J=249.0, 7.3, 6.2 Hz, 2C), 128.4 (dt, J=10.2, 3.82 Hz), 111.0 (ddd, J=18.9, 6.0, 3.5 Hz, 2C), 108.5 (dt, J=19.8, 10.5 Hz), 62.1 (d, J=6.5 Hz, 2C), 20.6 (dt, J=142.1, 2.3 Hz), 16.0 (d, J=6.2 Hz, 2C). $^{31}$P {$^1$H} NMR (161.97 MHz, DMSO): δ 24.68. Analysis calculated (found) %: C 50.01 (49.71), H 5.72 (5.78). MS (FAB, m/z): 265 (M+, 100%). Exact mass calculated (found) for [M+H]+, m/z): 265.08051 (265.08278).

Synthesis of 2,6-difluorobenzylphosphonic acid

Diethyl 2,6-difluorobenzylphosphonate (2.00 g, 7.57 mmol) was dissolved in dry dichloromethane (20 mL). Bromotrimethylsilane (3.3 mL, 25 mmol) was added via syringe. The reaction was capped with a greased glass stopper and allowed to stir for 6 hours. The volatiles were removed under reduced pressure to yield a yellow oil. This was dissolved in 10:1 methanol:water (20 mL) and allowed to stir overnight. After removing the solvents, recrystallization in acetonitrile yielded a white crystalline solid (1.199 g, 76% yield). $^1$H NMR (400.14 MHz, DMSO) δ 7.29 (m), 7.04 (m, 2H), 2.96 (d, J=20.99 Hz, 2H). $^{31}$P {$^1$H} NMR (161.97 MHz, DMSO): δ 19.51. Analysis calculated (found) %: C 40.40 (40.64), H 3.39 (3.34).

Synthesis of diethyl 2,6-difluorophenylphosphonate 2,6-difluoroiodobenzene (3.0 g, 12.5 mmol) was combined with triethylphosphite (10.7 mL, 62.5 mmol) in a pressure vessel which had been flushed with nitrogen. The vessel was sealed and rotated in the photoreactor (16 bulbs —350 nm) for 20 hours. The reaction mixture was put under hi-vacuum (0.08 Torr) at 50° C. for 5 hours. A column was run in hexanes and ethyl acetate (increasing polarity as run). The top spot, which was UV active, was separated. After removing solvent, a yellow-tinted liquid was left (2.30 g, 74% yield). $^1$H NMR (400.14 MHz, DMSO) δ 7.72 (m), 7.21 (m, 2H), 4.10 (m, 4H), 1.25 (t, J=7.04 Hz). $^{31}$P {$^1$H} NMR (161.97 MHz, DMSO): δ 8.23. The phosphonate can be hydrolyzed as described above to provide the corresponding phosphonic acid.

Synthesis of 4-fluorophenylphosphonic acid

Diethyl 4-fluorophenylphosphonate (600 mg, 2.55 mmol) was combined with 8M HCl (10 mL, excess) and the mixture refluxed overnight. The reaction was cooled and filtered to remove dark specks. The solvent was removed under vacuum until a solid began to form. The mixture was then put in the refrigerator for several hours. The solid was dried to yield an off-white powder (P80 mg). $^1$H NMR (400.14 MHz, DMSO) δ 7.71 (ddd, J=12.49, 8.52, 5.99 Hz, 2H), 7.28 (ddd, J=9.02, 9.02, 2.65 Hz, 2H). $^{31}$P{$^1$H} NMR (161.97 MHz, DMSO): δ 12.81. Analysis calculated (found) %: C 40.93 (40.33), H 3.43 (3.49).

The filtrate was dried under vacuum to yield a beige powder (250 mg). Analysis calculated (found) %: C 40.93 (39.47), H 3.43 (3.48).

Synthesis of perfluorophenylphosphonic acid

Diethyl perfluorophenylphosphonate (1060 mg, 3.48 mmol) was combined with 8M HCl (10 mL, excess) and the mixture refluxed overnight. The reaction was cooled and filtered to remove dark specks. The solvent was removed under vacuum until a solid began to form. The mixture was then put in the refrigerator for several hours. The solid was dried to yield an off-white powder (130 mg). $^1$H NMR showed no signal other than the DMSO. $^{31}$P {$^1$H} NMR (161.97 MHz, DMSO): δ −0.93. Analysis calculated (found) %: C 29.05 (29.89), H 0.81 (1.02).

The filtrate was dried under vacuum to yield a beige powder (740 mg). Analysis calculated (found) %: C 29.05 (29.33), H 0.81 (0.95).

Device Efficiency

OLED devices were fabricated with ITO electrodes having surface bound phosphonic acids (PA). The phosphonic acid modified ITO samples were then transferred for loading into the evaporation chamber through the T-antechamber that connects the double glove box in line with the evaporation chamber. First, a hole transport layer (HTL) of N,N'-diphenyl-N, N'-bis(1-naphthyl)-1,1' biphenyl-4,4"diamine (α-NPD) (40 nm) was deposited at the rate of 1 Å/s by thermal evaporation. An emitting layer was formed by coevaporation of (6 wt %) fac tris(2-phenylpyridinato-N,$C^{2'}$) iridium [Ir(ppy)$_3$] in 4,4'-di(carbazol-9-yl)-biphenyl (CBP) to give a 20 nm-thick film. The evaporation rate at the substrate was 1 Å/s. A hole blocking layer of bathocuproine (2,9-dimethyl-4,7-diphenyl-1,10-phenanthroline, BCP) (40 nm) was subsequently deposited over the emissive layer at a rate of 0.4 Å/s. During the deposition of the organic layers, the pressure was kept below $1 \times 10^{-7}$ Torr. Finally a thin layer of lithium fluoride (LiF, 3 nm) acting as an electron injection layer followed by Al (200 nm) as cathode were deposited. LiF and Al were deposited, at pressures below $1 \times 10^{-6}$ Torr and at rates of 0.1 Å/s and 2 Å/s, respectively. A shadow mask was used for Al deposition to make five devices per substrate with an active area of 0.1 cm$^2$ for each device. The final configuration of the device was Glass/ITO/Monolayer/α-NPD(40 nm)/CBP:Ir(ppy)$_3$(20 nm)/BCP (40 nm)/LiF(3 nm)/Al (200 nm).

The current-voltage-light (I-L-V) characteristics were measured in the glove box without exposing the devices to air.

Figure 6:
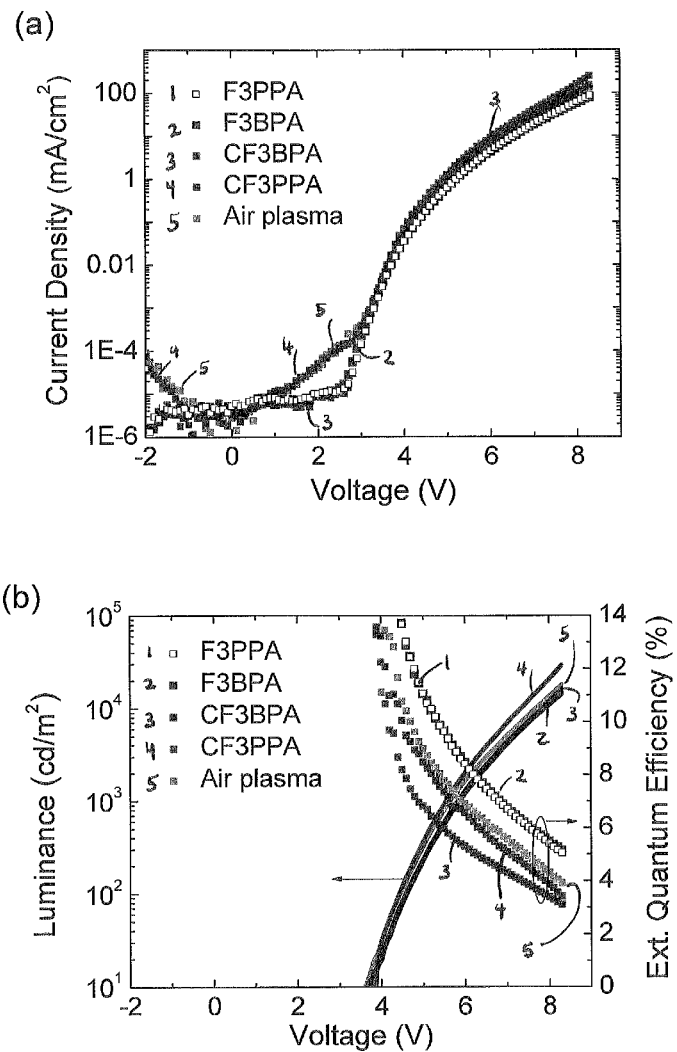
FIG. 6 shows (a) the current-voltage (I-V), and (b) the luminance/external quantum efficiency (EQE) graphs of OLED devices fabricated with ITO with surface-bound phosphonic acids compared to devices with ITO treated with air plasma.
Figure 7:
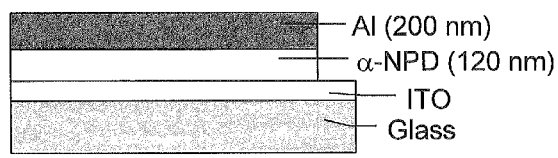
FIG. 7 shows the structure of the single layer diode and current-voltage (IV) graph for the diode fabricated with ITO with surface-bound phosphonic acids compared to devices with ITO treated with air plasma.
Figure 7:
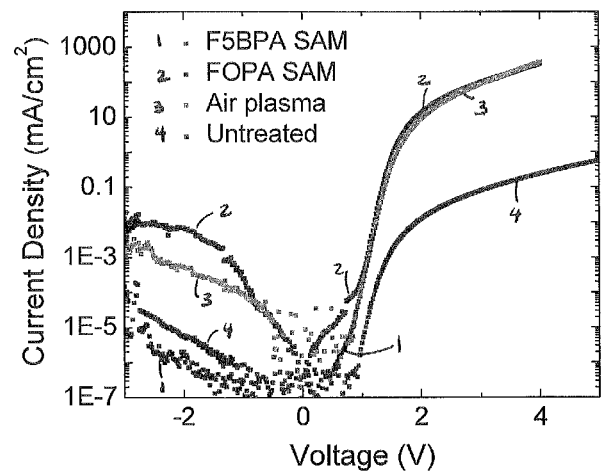

The devices showed the very similar efficiency compared to devices fabricate with air plasma treated ITO (FIG. 6, see Table 1 for the structures reference in FIG. 6); however, since the work function was more stable with the fluorinated aryl phosphonic acid treated ITO than with the air plasma treated ITO, the fabrication was more facile.

TABLE 2

Figure 8:
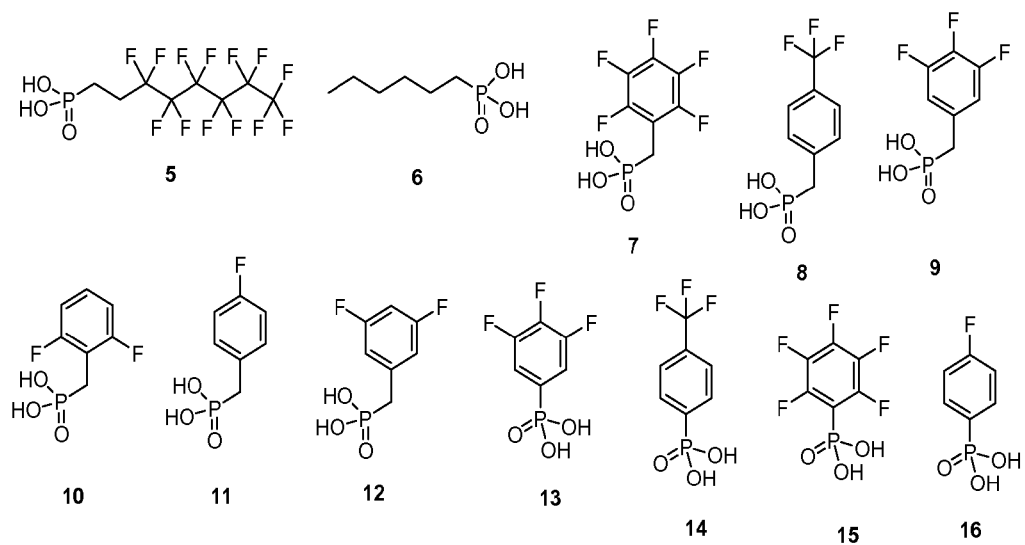
FIG. 8 shows some phosphonic acids.

Values of the work functions and valence band maximas (VBMs) for the compounds presented in FIG. 8. Entry 1 = DSC ITO; Entry 2 = DSC OP ITO-2; Entry 3 = DSC OP-ITO-2; Entry 4 = DSC OP-ITO-3. DSC ITO is detergent/solvent cleaned ITO (see below), DSC OP-ITO is DSC ITO plus 15 minutes of OP etching. All the other samples are OP-ITO modified with the PA shown. The numbers in the Sample column reference the compounds in FIG. 8. In some cases OP increases the coverage of the monolayer and affects surface energies and work function differently than DSC alone.

| Compound # | Work Function (eV) (+/−0.1 eV) | VBM (eV) (+/−0.1 eV) |
|---|---|---|
| 1 | 4.5 | 3 |
| 2 | 5.5 | 2.9 |
| 3 | 5.5 | 2.7 |
| 4 | 5.8 | 2.7 |
| 5 | 5.6 | 3.1 |
| 6 | 4.9 | 2.9 |
| 7 | 5.2 | 3.1 |
| 8 | 5.6 | 2.7 |
| 9 | 5.3 | 2.8 |
| 10 | 4.4 | 3.1 |
| 11 | 5.0 | 2.9 |
| 12 | 5.2 | 2.9 |
| 13 | 5.4 | 3.0 |
| 14 | 5.6 | 3.0 |
| 15 | 5.1 | 3.1 |
| 16 | 5.0 | 3.0 |

Figure 9:
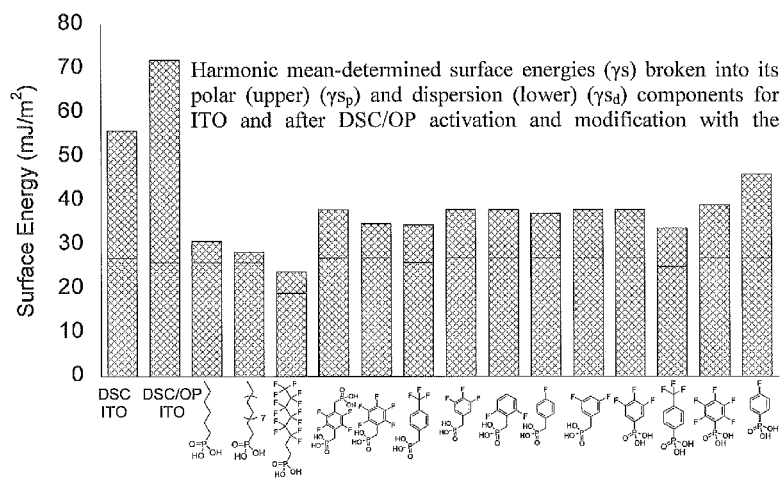
FIG. 9 shows the surface energies of some phosphonic acids bound to the surface of a metal oxide.

FIG. 9 shows the surface energy graph of the various samples (listed above). The upper, blue portion is the polar component and the lower, orange portion is the dispersive component. FIG. 9 shows the surface energy of some of the phosphonic acids in Table 2 bound to the surface of ITO.

TABLE 3

Number of fluorines, ratio of the areas of the F1s peak to the In3p peak, the adjusted ratio (taking the number of fluorines on the molecule into account), and the relative ratios (by setting one of the adjusted ratios to 1.00, and adjusting the others in a likewise fashion. The numbers in the Sample column reference the compounds in FIG. 8.

| Sample | # F | ratio F1s/In3p | adjusted ratio | relative ratio |
|---|---|---|---|---|
| 7 | 5 | 0.188 | 37.6 | 0.75 |
| 8 | 3 | 0.155 | 51.7 | 1.03 |
| 9 | 3 | 0.157 | 52.3 | 1.05 |
| 10 | 2 | 0.065 | 32.5 | 0.65 |
| 11 | 1 | 0.050 | 50.0 | 1.00 |
| 12 | 2 | 0.088 | 44.0 | 0.88 |
| 13 | 3 | 0.150 | 50.0 | 1.00 |
| 14 | 3 | 0.170 | 56.7 | 1.13 |
| 15 | 5 | 0.188 | 37.6 | 0.75 |
| 16 | 1 | 0.025 | 25.0 | 0.50 |

By calculating the areas of the F1s and In3p(3/2) peaks and comparing them to one another, a general picture can be seen as to how good of a monolayer each PA yielded with respect to one-another (Table 5). However, several things should be taken into account. First of all, the intensities should all be adjusted to take into account the number of fluorines on each modifier. Additionally, those modifiers which have ortho-substituted fluorines may show decreased relative ratios because of the direction in which the fluorines are pointing. Because these atoms may be shielded from the X-rays, their intensity may be less than expected.

Figure 10:
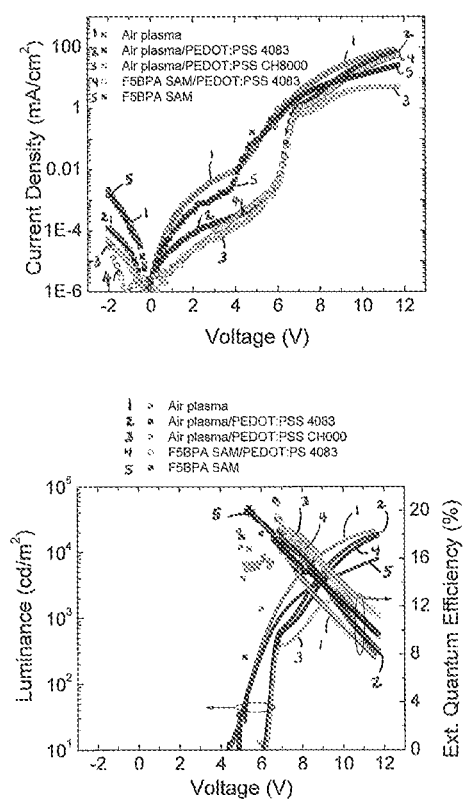
FIG. 10 shows (a) the current-voltage (I-V), and (b) the luminance/external quantum efficiency (EQE) graphs for OLED devices fabricated with ITO with surface-bound phosphonic acids compared to devices with ITO-PEDOT:PSS.
Figure 11:
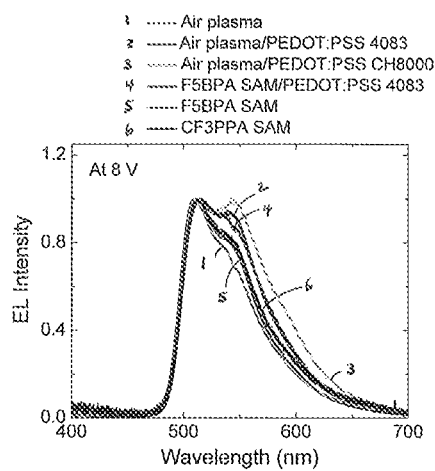
FIG. 11 shows the electroluminescence (EL) spectra for OLED devices fabricated with ITO with surface-bound phosphonic acids compared to devices with ITO-PEDOT:PSS.

FIG. 10 shows the IV and luminance/EQE graphs for OLED devices fabricated with ITO with surface-bound phosphonic acids compared to devices with ITO-PEDOT:PSS (20 nm). The efficiencies of the devices at 1000 cd/m$^2$ are 20%, 18.9%, 17%, and 17.8% for air plasma, PEDOT:PSS 4083 (CLEVIOS PVP AI 4083, formerly Baytron, Lot#HCD07P109), PEDOT:PSS CH8000 (CLEVIOS PVP CH 8000, formerly Baytron, Lot #BPSV0003), for F5BPA. The electroluminescent spectra of devices fabricated with ITO with surface-bound phosphonic acids and ITO-PEDOT are shown in FIG. 11. The electroluminescent spectra for PEDOT devices are modified compared to the air plasma and phosphonic acid bound ITO devices. This modification affects the color output of the device. Thus, ITO phosphonic acid electrodes have the nearly the same efficiency of air plasma and PEDOT devices without the work function stability issues of air plasma and the color modification of PEDOT.

Figure 12:
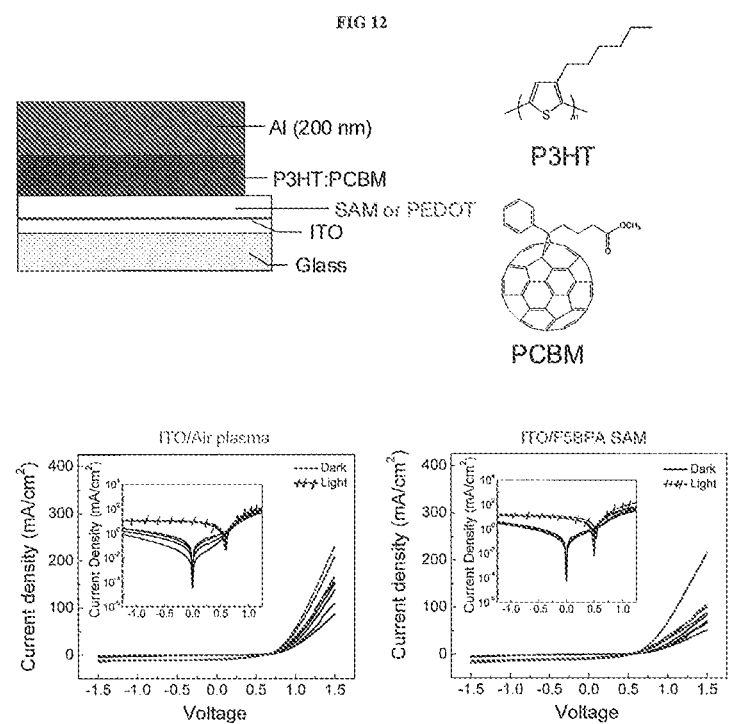
FIG. 12 shows the structure of the organic photovoltaic device (OPV) and the current-voltage (IV) graphs for OPV devices fabricated with ITO with surface-bound phosphonic acids compared to OPV devices with ITO treated with air plasma.
Figure 13:
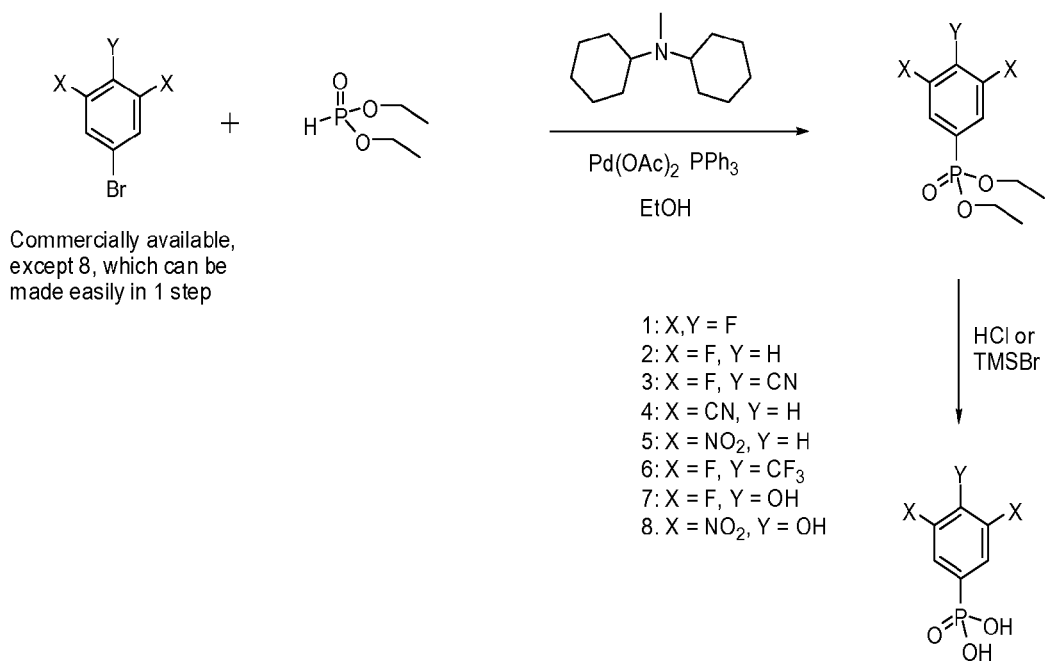
FIG. 13 shows some other phosphonic acids and methods of synthesis.

An organic photovoltaic (OPV) device (FIG. 12) was fabricated on phosphonic acid (PA) modified ITO electrode. For comparison, the OPV devices based on air plasma treatment were also fabricated. A bulk-heterojunction layer (100 nm) based on poly__3-hexylthiophene (P3HT) and __6,6__-phenyl C71 butyric acid methyl ester (PCBM-70) was spin coated from chlorobenzene solution (17 mg/ml in ratio of 10:7:: P3HT:PCBM at 700 RPM, for 1 min. The aluminum electrodes were deposited on the top of P3HT:PCBM layer by using thermal evaporation at a pressure below $1 \times 10^{-6}$ Torr and the rate of 2 Å/s. A shadow mask was used for Al deposition to make five devices per substrate with an active area of 0.1 cm$^2$ for each device. The samples were then annealed at 150° C. on the hot plate for 30 min. under nitrogen environment. FIG. 12 shows the dark and light IV graphs for plasma treated ITO devices and phosphonic acid treated device with lamp intensity of 71.5 mW/cm$^2$. The device parameters listed in Table 4 are averages for three devices each.

TABLE 4

Performance data for OPV devices.

| Sample | $V_{oc}$ (V) | $J_{sc}$ (mA/cm$^2$) | FF | η (%) | $R_s$A (Ω cm$^2$) | $R_p$A (Ω cm$^2$) |
|---|---|---|---|---|---|---|
| Air plasma-ITO | 0.588 | −9.3 | 0.34 | 2.6 | 2.9 | 198 |
| F5BPA Monolayer | 0.505 | −8.2 | 0.33 | 2.0 | 6.2 | 129 |

Synthesis of Functionalized Phosphonic Acids

Synthesis of 2-(12-bromododecyl)isoindoline-1,3-dione 1,12-dibromododecane (32.22 g, 98.2 mmol), potassium phthalimide (4.60 g, 24.5 mmol), and dimethylformamide (20 mL) were combined and refluxed at 160° C. for 2.5 hours. Upon cooling, water was added and the organic taken into dichloromethane (separated on a separatory funnel). The solvent was evaporated under reduced pressure and the crude product was columned in hexanes. The spots were not separated, and the fractions were combined, the solvent removed, and the crude material re-dissolved in 300 mL acetone. This was refluxed, and 10 g potassium phthalimide was added over 4 hours. The mixture was refluxed overnight. After cooling and removing the solvent, the crude product was columned using 1:1 ethyl acetate:hexanes. The top spot proved to be the desired product, which was collected as a white solid (9.30 g) that matched the reported literature: *Helv. Chimica Acta.* 2001, 84(3), 678-689.

Synthesis of diethyl 12-(1,3-dioxoisoindolin-2-yl)dodecylphosphonate 2-(12-bromododecyl)isoindoline-1,3-dione (9.30 g, 23.6 mmol) was combined with triethylphosphite (11.76 g, 70.7 mmol) in a round bottom flask and the mixture heated and stirred at 135° C. for 16 hours. The reaction mixture was then put under hi-vacuum at 90° C. for 4 hours. The product was then obtained as a clear oil after column chromatography in ethyl acetate. (8.96 g, 84% yield). $^1$H NMR (400.14 MHz, CDCl$_3$) δ 7.80 (dd, J=5.43, 3.04 Hz, 2H), 7.67 (dd, J=5.47, 3.05 Hz, 2H), 4.08-4.02 (m, 4H), 3.63 (t, J=7.33 Hz, 2H), 1.73-1.45 (m, 6H), 1.32-1.11 (m, 22H). $^{13}$C {$^1$H} NMR (100.62 MHz, CDCl$_3$) δ 168.4 (2C), 133.7 (2C), 132.1 (2C), 123.0 (2C), 61.30 (d, J=6.5 Hz, 2C), 37.96, 30.51, (d, J=17.0 Hz), 29.41 (2C), 29.35, 29.25, 29.07, 28.98, 28.49, 26.75, 25.55 (d, J=140.1 Hz), 22.29 (d, J=5.0 Hz), 16.39 (d, J=6.1 Hz, 2C). $^{31}$P {$^1$H} NMR (161.97 MHz, CDCl$_3$): δ 33.38. MS (ESI, m/z): 452.235 (M$^{+,}$ 100%). Exact mass calculated (found) for [M+H]$^+$, m/z): 452.256039 (452.254800). Analysis calculated (found) %: C 63.84 (63.41), H 8.48 (8.53).

Synthesis of 12-(1,3-dioxoisoindolin-2-yl)dodecylphosphonic acid

Diethyl 12-(1,3-dioxoisoindolin-2-yl)dodecylphosphonate (2.00 g, 4.43 mmol) was dissolved in dry dichloromethane (25 mL). Bromotrimethylsilane (1.8 mL, 14.2 mmol) was added via syringe. The reaction was capped with a greased glass stopper and allowed to stir overnight. The volatiles were removed under reduced pressure to yield a yellow oil. This was dissolved in 10:1 methanol:water (20 mL) and allowed to stir overnight. After removing the solvents, recrystallization in acetonitrile yielded a white powdery solid (1.709 g, 98% yield). $^1$H NMR (400.14 MHz, DMSO) δ 7.84 (m, 4H), 3.54 (t, J=7.1 Hz, 2H), 1.58-1.53 (m, 2H), 1.50-1.31 (m, 4H), 1.30-1.20 (m, 16H). $^{13}$C {$^1$H} NMR (100.62 MHz, DMSO) δ 167.9 (2C), 134.4 (2C), 131.6 (2C), 123.0 (2C), 37.36, 30.08 (d, J=15.8 Hz), 28.99, 28.95, 28.87 (2C), 28.70, 28.53, 27.85, 27.54 (d, J=136.5 Hz), 26.22, 22.73, (d, J=4.58 Hz). $^{31}$P {$^1$H} NMR (161.97 MHz, DMSO): δ 27.74. MS (FAB, m/z): 396.2 (M$^{+,}$ 100%). Exact mass calculated (found) for [M+H]$^+$, m/z): 396.19399 (396.19445). Analysis calculated (found) %: C 60.75 (60.64), H 7.65 (7.80).

Synthesis of 11-phosphonoundecanoic acid 11-methoxy-11-oxoundecylphosphonic acid (1.72 g, 6.136 mmol) was dissolved in 8M HCl (25 mL, excess) and the mixture refluxed overnight. Upon cooling, a white crystalline solid precipitated. This was filtered and washed with cold acetonitrile. The filtrate was reduced and the precipitate that formed was also collected by filtration (1.156 g, 71% yield).

The synthesis of 3-(4-benzoylphenoxy)propylphosphonic acid was synthesized according to the literature.

Synthesis of a Phosphonic Acid Comprising a Triaryl Amine

Figure 17:
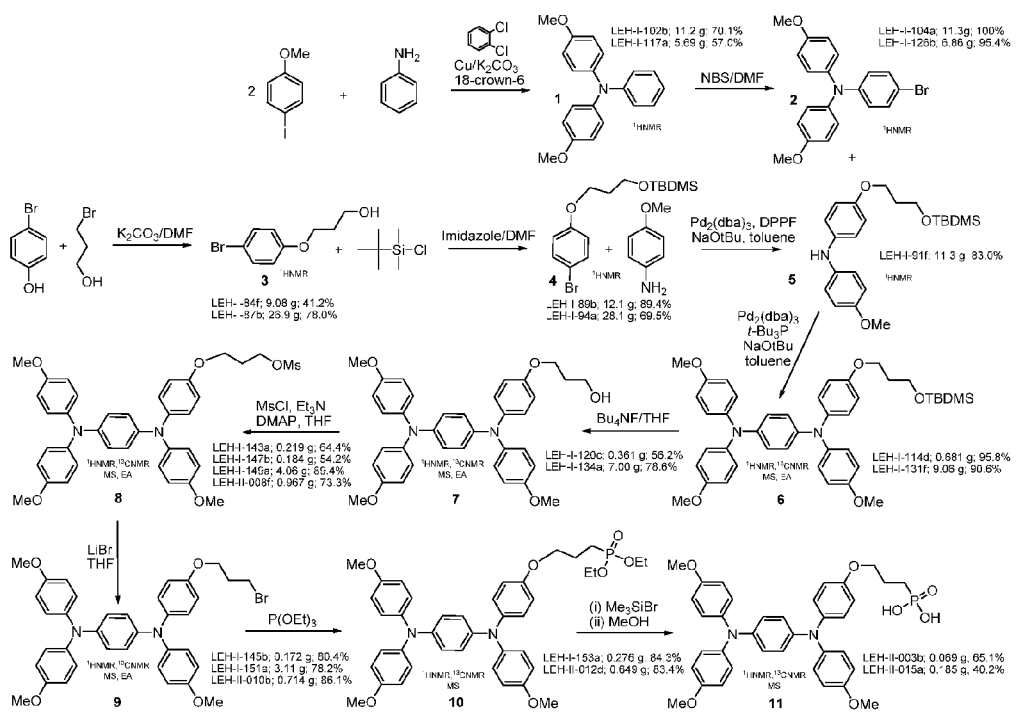
FIG. 17 outlines the synthesis of a phosphonic acid comprising a triarylamine group.

The following synthetic procedures are in reference to FIG. 17.

Synthesis of N,N-bis(4-methoxyphenyl)aniline. Freshly distilled aniline (4.84 g, 52.0 mmol), p-iodoanisole (30.4 g, 130.0 mmol), powdered anhydrous potassium carbonate (57.5 g, 416.0 mmol), electrolytic copper powder (13.3 g, 208.0 mmol), and 18-crown-6 (2.75 g, 10.4 mmol) were added to a dry, three necked round bottom flask under nitrogen. The mixture was refluxed in 100 mL o-dichlorobenzene 18 h (during which time some solvent evaporated). Ethyl acetate (250 mL) was added to the reaction flask. The resulting mixture was filtered to remove copper and organic salts and the solvent was removed under reduced pressure. The product was purified by washing with methanol to yield a tan solid (11.2 g, 70.1%). $^1$H NMR (300 MHz, CDCl$_3$) δ 7.16 (m, 2H), 7.01 (d, J=9.0 Hz, 4H), 6.78 (d, J=9.0 Hz, 4H), 6.83 (t, J=1.5 Hz, 2H), 6.81 (t, J=1.5 Hz, 1H), 3.55 (s, 6H).

Synthesis of 4-bromo-N,N-bis(4-methoxyphenyl)aniline. 2. N,N-bis(4-methoxyphenyl)aniline 1 (9.0 g, 29.5 mmol) was dissolved in 100 mL dimethylformamide in a 250 mL round bottom flask. N-bromosuccinimide (5.25 g, 29.5 mmol) was dissolved in 30 mL dimethylformamide and added dropwise to the reaction mixture. The reaction was allowed to stir at room temperature while being monitored by thin layer chromatography (TLC) (Reaction Time=23 h). The reaction mixture was quenched using 600 mL water and extracted with 4×150 mL dichloromethane. The organic layers were combined and washed with 4×150 mL saturated sodium thiosulfate solution and dried over sodium sulfate. The solvent was removed under reduced pressure. The product was purified along with materials prepared previously using flash chromatography on silica gel eluting with 5:1 hexanes:ethylacetate (12.1 g, 100%). $^1$H NMR (300 MHz, CDCl$_3$) δ 7.28 (d, J=9.0 Hz, 2H), 7.05 (d, J=9.0 Hz, 4H), 6.90 (d, J=9.0 Hz, 4H), 6.73 (d, J=9.0 Hz, 2H), 3.77 (s, 6H).

Synthesis of 3-(4-bromophenoxy)propan-1-ol. To a 250 mL round bottom flask was added 4-bromophenol (16.5 g, 95.3 mmol), 3-bromopropanol (15.9 g, 114.4 mmol), N,N-dimethylformamide (50 mL) and potassium carbonate (22.4 g, 162.0 mmol). The reaction was allowed to stir at room temperature while being monitored by TLC(CH$_2$Cl$_2$). Upon the disappearance of 4-bromophenol the mixture was poured into a separatory funnel containing 50 mL of water. The product was extracted in diethyl ether and the organic layer was washed with 3×25-mL portions of cold water. The solvent was removed under reduced pressure. The product was purified by flash chromatography on silica gel eluting with dichloromethane. The solvent was removed under reduced pressure. Residual solvent and remaining 3-bromopropanol were removed in vacuo (14.2 g, 64.4%). $^1$H NMR (300 MHz, CDCl$_3$) δ 7.35 (d, 9.0 Hz), 6.77 (d, J=9.0 Hz, 2H), 4.06 (t, J=6.0 Hz, 2H), 3.84 (t, J=6.0 Hz, 2H), 2.10 (q, J=6.0 Hz, 2H), 1.65 (s, 1H).

Synthesis of (3-(4-bromophenoxy)propoxy)(tert-butyl)dimethylsilane. To a dry 100 mL round bottom flask under nitrogen was added 3-(4-bromophenoxy)propan-1-ol (9.0 g, 39.0 mmol), tert-butyldimethylsilyl chloride (7.0 g, 47.0 mmol), imidizole (3.2 g, 47.0 mmol), and 20 mL of N,N-dimethylformamide. The reaction was allowed to stir at room temperature while being monitored by thin layer chromatography. Upon disappearance of the starting material the reaction mixture was poured into a separatory funnel containing 50 mL of cold water. The product was extracted using 3×25 mL ether. The organic layers were combined and washed with 3×25 mL cold water and 3×25 mL saturated sodium chloride solution. The resulting organic layer was dried over magnesium sulfate, filtered from drying agent, and the solvent was removed under reduced pressure. The material was purified by filtering through a plug of silica gel eluting with 4:6 dichloromethane:hexane. The solvent was removed under reduced pressure (12.1 g, 89.4%). $^1$H NMR (300 MHz, CDCl$_3$) δ 7.34 (d, J=9.0 Hz, 2H), 6.76 (d, J=9.0 Hz, 2H), 4.00 (t, J=6.0 Hz, 2H), 3.76 (t, J=6.0 Hz, 2H), 1.95 (q, J=6.0 Hz, 2H), 0.87 (s, 9H), 0.03 (s, 6H).

Synthesis of 4-(3-(tert-butyldimethylsilyloxy)propoxy)-N-(4-methoxyphenyl)aniline. 5. To a dry 500 mL round bottom flask under nitrogen was added (3-(4-bromophenoxy)propoxy)(tert-butyl)dimethylsilane (12.1 g, 35.0 mmol), 4-anisidine (5.17 g, 42.0 mmol), and 20 mL anhydrous toluene. The mixture was degassed for 10 minutes before addition of dibenzylideneacetone di palladium Pd$_2$(dba)$_3$ (0.64 g, 0.70 mmol), 1,1'-Bis(diphenylphosphino)ferrocene (DPPF) (0.68 g, 1.2 mmol), and 20 mL anhydrous toluene. After 10 minutes of mixing, sodium tert-butoxide (4.7 g, 49.0 mmol) was added with 10 mL anhydrous toluene. The reaction mixture was heated to 90° C. and allowed to stir overnight while being monitored by thin layer chromatography. Upon disappearance of the starting material the reaction mixture was filtered through a plug of silica gel eluting with dichloromethane (Reaction Time=22 h). The product was purified by flash chromatography (silica gel, 5:1 hexanes:ethyl acetate). The solvent was removed under reduced pressure. The residual solvent was removed in vacuo (11.3 g, 83.0%). $^1$H NMR (300 MHz, CDCl$_3$) δ 7.06 (d, J=3.3 Hz, 2H), 7.03 (d, J=3.3 Hz, 2H), 6.91 (d, J=3.3 Hz, 2H), 6.88 (d, J=3.3 Hz, 2H), 6.85 (s, 1H), 4.10 (t, 6.3 Hz, 2H), 3.90 (t, J=6.0 Hz, 2H), 3.81 (s, 3H), 2.01 (q, J=6.3 Hz, 2H), 0.97 (s, 9H), 0.14 (s, 6H).

Synthesis of N1-(4-(3-(tert-butyldimethylsilyloxy)propoxy)phenyl)-N1,N4,N4-tris(4-methoxyphenyl)benzene-1,4-diamine.6. Anhydrous toluene (30.0 mL) was degassed by sparging with nitrogen for 10 minutes in a dry 200 mL schlenk flask. Tri(tert-butyl) phosphine (0.187 g; 0.924 mmol) and Pd$_2$(dba)$_3$ (0.283 g, 0.309 mmol) were added and the mixture was allowed to stir. After 10 minutes, 4-bromo-N,N-bis(4-methoxyphenyl)aniline (5.92 g; 15.4 mmol), 4-(3-(tert-butyldimethylsilyloxy)propoxy)-N-(4-methoxyphenyl)aniline (6.00 g; 15.4 mmol), and sodium tert-butoxide (2.08 g, 21.6 mmol) were added. The reaction was allowed to stir at 90° C. while being monitored by TLC (5:1 hexanes:ethyl acetate). Upon the disappearance of the starting materials the mixture was filtered through Celite eluting with ethyl acetate. The product was purified by flash chromatography (silica gel, 5:1 hexanes:ethyl acetate). The solvent was removed under reduced pressure. The residual solvent was removed in vacuo (9.06 g, 90.6%). $^1$H NMR (300 MHz, C$_3$D$_6$O) δ 6.98 (m, 8H), 6.86 (m, 8H), 6.82 (s, 4H), 4.06 (t, J=6.3 Hz, 2H), 3.83 (t, J=6.3 Hz, 2H), 3.76 (s, 9H), 1.95 (q, J=6.0 Hz, 2H), 0.890 (s, 9H), 0.058 (s, 6H). $^{13}$C {$^1$H} NMR (300 MHz, C$_3$D$_6$O, δ): 156.40, 155.83, 143.65, 142.31, 126.24, 123.78, 116.04, 115.41, 65.28, 60.09, 55.63, 33.27, 26.23, −5.27. HRMS-EI (m/z): [M]$^+$ calcd for C$_{42}$H$_{50}$N$_2$O$_5$Si, 690.35; found, 690.6). Anal. Calcd for C$_{42}$H$_{50}$N$_2$O$_5$Si: C, 73.01; H, 7.29; N, 4.05. Found: C, 73.25; H, 7.43; N, 4.01.

Synthesis of 3-(4-((4-(bis(4-methoxyphenyl)amino)phenyl)(4-methoxyphenyl)amino)phenoxy)propan-1-ol. 7. To a dry 250 mL round bottom flask under nitrogen was added N1-(4-(3-(tert-butyldimethylsilyloxy)propoxy)phenyl)-N1,N4,N4-tris(4-methoxyphenyl)benzene-1,4-diamine (9.06 g, 13.1 mmol), tetrahydrofuran (12.4 mL), and tetrabutylammonium fluoride (8.21 g, 31.4 mmol). The reaction was allowed to stir at room temperature while being monitored by thin layer chromatography. Upon disappearance of the starting material the reaction mixture was poured into a separatory funnel containing 150 mL of cold water. The product was extracted using 3×75 mL ether. The organic layers were combined and dried over MgSO$_4$. The drying agent was removed by filtration and the solvent was removed under reduced pressure. The material was purified by flash chromatography (silica gel, 1:2 hexanes:ethyl acetate) and recrystallization (methanol) to yield a white solid (5.93 g, 78.6%). $^1$H NMR (400 MHz, C$_3$D$_6$O) δ 6.97 (m, 8H), 6.85 (m, 8H), 6.81 (s, 4H), 4.07 (t, J=6.3 Hz, 2H), 3.78 (s, 9H), 3.71 (q, J=5.7 Hz, 2H), 3.63 (t, J=5.2 Hz, 2H), 1.93 (q, J=6.3 Hz, 2H). $^1$H NMR (400 MHz, C$_3$D$_6$O with D$_2$O) δ 6.95 (m, 8H), 6.84 (m, 8H), 6.79 (s, 4H), 4.03 (t, J=6.3 Hz, 2H), 3.74 (s, 9H), 3.68 (t, J=6.2 Hz, 2H), 1.92 (q, J=6.3 Hz, 2H). $^{13}C\{^1H\}$ NMR (400 MHz, $C_3D_6O$) δ 156.29, 155.77, 143.59, 143.53, 142.22, 142.13, 126.17, 123.68, 123.64, 115.98, 115.37, 65.74, 58.80, 55.62, 33.11. HRMS-EI (m/z): [M]$^+$ calcd for $C_{36}H_{36}N_2O_5$, 576.26; found, 576.4). Anal. Calcd for $C_{36}H_{36}N_2O_5$: C, 74.98; H, 6.39; N, 4.86. Found: C, 74.80; H, 6.25; N, 4.82.

Synthesis of 3-(4-((4-(bis(4-methoxyphenyl)amino)phenyl)(4-methoxyphenyl)amino)phenoxy)propyl methanesulfonate. To a dry schlenk flask was added 3-(4-((4-(bis(4-methoxyphenyl)amino)phenyl)(4-methoxyphenyl)amino) phenoxy)propan-1-ol (1.16 g, 2.01 mmol) and 4-dimethylaminopyridine (0.012 g, 0.100 mmol. The flask was evacuated under vacuum and filled with nitrogen before addition of anhydrous tetrahydrofuran (2.0 mL). The mixture was placed in an ice bath and allowed to stir for 10 minutes. Triethylamine (0.712 g, 7.04 mmol) was added and the reaction was allowed to stir for 10 minutes. Added methanesulfonyl chloride (0.691 g, 6.03 mmol) and allowed mixture to stir for 5 minutes. The ice bath was removed and the mixture was stirred at room temperature while being monitored by thin layer chromatography (1:2 hexanes:ethyl acetate). Upon disappearance of the starting material the reaction mixture was poured into a separatory funnel containing 100 mL of cold water. The product was extracted using 3×50 mL ether. The organic layers were combined and washed with 3×50 mL of water, sodium bicarbonate solution, and sodium chloride solution. The resulting ether layers were dried over $MgSO_4$. The drying agent was removed by filtration and the solvent was removed under reduced pressure. The residual solvent was removed in vacuo. The material was purified by flash chromatography (silica gel, 4:2 toluene:ethyl acetate) to yield an off-white solid (0.967 g, 73.3%). $^1H$ NMR (400 MHz, $C_3D_6O$) δ 6.96 (m, 8H), 6.85 (m, 8H), 6.80 (s, 4H), 4.43 (t, J=6.3 Hz, 2H), 4.09 (t, J=6.0 Hz, 2H), 3.74 (s, 9H), 3.09 (s, 3H), 2.19 (q, J=6.2 Hz, 2H). $^{13}C\{^1H\}$ NMR (400 MHz, $C_3D_6O$) δ 156.42, 156.39, 155.30, 143.73, 143.49, 142.62, 142.26, 142.22, 126.33, 126.28, 126.00, 123.91, 123.69, 116.14, 115.41, 67.94, 64.61, 55.63, 36.97, 29.87. HRMS-EI (m/z): [M]$^+$ calcd for $C_{37}H_{38}N_2O_7S$, 654.24; found, 654.1). Anal. Calcd for $C_{37}H_{38}N_2O_7S$: C, 67.87; H, 5.85; N, 4.28. Found: C, 67.61; H, 5.77; N, 4.26.

Synthesis of N1-(4-(3-bromopropoxy)phenyl)-N1,N4,N4-tris(4-methoxyphenyl)benzene-1,4-diamine. 9. To a dry schlenk flask was added 3-(4-((4-(bis(4-methoxyphenyl) amino)phenyl)(4-methoxyphenyl)amino)phenoxy)propyl methanesulfonate (4.06 g, 6.20 mmol). The flask was evacuated under vacuum and filled with nitrogen. Lithium bromide (5.39 g; 62.0 mmol) and tetrahydrofuran (6.2 mL) were added under nitrogen. The mixture was allowed to stir at 60° C. overnight. Upon disappearance of the starting material the reaction mixture was poured into a separatory funnel containing 100 mL of cold water. The product was extracted using 3×50 mL ether. The organic layers were combined and washed with 3×50 mL of water. The resulting ether layers were dried over $Na_2SO_4$. The drying agent was removed by filtration and the solvent was removed under reduced pressure. The residual solvent was removed in vacuo (3.12 g, 78.2%). $^1H$ NMR (400 MHz, $C_3D_6O$) δ 6.97 (m, 8H), 6.86 (m, 8H), 6.80 (s, 4H), 4.09 (t, J=5.9 Hz, 2H), 3.75 (s, 9H), 3.66 (t, J=6.6 Hz, 2H), 2.28 (q, J=6.2 Hz, 2H). $^{13}C\{^1H\}$ NMR (400 MHz, $C_3D_6O$) δ 156.39, 155.34, 143.71, 143.51, 142.22, 127.05, 126.27, 126.03, 123.90, 123.70, 116.10, 115.40, 114.61, 66.34, 55.62, 33.25, 31.05. HRMS-EI (m/z): [M]$^+$ calcd for $C_{36}H_{35}BrN_2O_4$, 640.18; found, 640.1). Anal. Calcd for $C_{36}H_{35}BrN_2O_4$: C, 67.60; H, 5.52; N, 4.38. Found: C, 67.43; H, 5.61; N, 4.24.

Synthesis of diethyl 3-(4-(4-(bis(4-methoxyphenyl) amino)phenyl)(4-methoxyphenyl)amino)phenoxy)propylphosphonate. To a dry schlenk flask was added N1-(4-(3-bromopropoxy)phenyl)-N1,N4,N4-tris(4-methoxyphenyl) benzene-1,4-diamine (0.714 g, 1.12 mmol) and the flask was purged with nitrogen.

Triethylphosphite (1.12 mL) was added and the mixture was allowed to stir at 160° C. overnight. Upon disappearance of the starting material the solvent was removed under vacuum distillation. The product was purified by flash chromatography (silica gel; ethyl acetate) to yield a light yellow oil (0.649 g, 83.4%). $^1H$ NMR (400 MHz, $C_3D_6O$) δ 6.96 (m, 8H), 6.84 (m, 8H), 6.80 (s, 4H), 4.05 (m, 6H), 3.74 (s, 9H), 1.93 (m, 4H), 1.26 (t, J=7.0 Hz, 6H). $^{13}C\{^1H\}$ NMR (400 MHz, $C_3D_6O$) δ 156.36, 155.50, 143.64, 143.55, 142.41, 142.25, 126.22, 126.11, 123.80, 123.71, 116.10, 115.38, 68.35 (d, J=16.6 Hz), 61.70 (d, J=6.2 Hz), 23.52 (d, J=4.6 Hz), 22.61 (d, J=142 Hz), 16.73 (d, J=5.8 Hz). HRMS-EI (m/z): [M]$^+$ calcd for $C_{40}H_{45}N_2O_7P$, 696.30; found, 696.2). Anal. Calcd for $C_{40}H_{45}N_2O_7P$: C, 68.95; H, 6.51; N, 4.02. Found: C, 68.80; H, 6.46; N, 4.02.

3-(4-((4-(bis(4-methoxyphenyl)amino)phenyl)(4-methoxyphenyl)amino)phenoxy)propylphosphonic acid. 11. To a dry 25 mL round bottom flask under nitrogen was added diethyl3-(4-(((4-(bis(4-methoxyphenyl)amino)phenyl)(4-methoxyphenyl)amino)phenoxy)propylphosphonate (0.500 g, 0.718 mmol) and the flask was purged with nitrogen. Dichloromethane (1.00 mL) and bromotrimethylsilane (0.199 g, 2.30 mmol) were added under nitrogen and the mixture was allowed to stir at room temperature overnight. Upon disappearance of the starting material the solvent was removed through nitrogen purge. Residual solvent was removed in vacuo. Anhydrous methanol (8.00 mL) was added to the flask and allowed to stir at room temperature overnight. White solid was filtered from methanol through cannula filtration. Solid was washed using 3×5 mL anhydrous methanol and dried in vacuo. The product was collected under nitrogen atmosphere as a green solid (0.185 g, 40.2%). $^1H$ NMR (400 MHz, $(CD_3)_2SO$) δ 9.87 (s, 2H), 6.89 (m, 8H), 6.83 (m, 8H), 6.71 (s, 4H), 3.91 (m, 2H), 3.69 (s, 9H), 1.84 (m, 2H), 1.51 (m, 2H). $^{13}C\{^1H\}$ NMR (400 MHz, $(CD_3)_2S$, δ): 154.98, 154.40, 142.17, 140.91, 140.77, 125.27, 125.19, 122.72, 122.68, 115.37, 114.82, 68.35 (m), 55.24, 23.62 (m). $^{31}P$ NMR (400 MHz, $(CD_3)_2S$, δ): 25.05. HRMS-EI (m/z): [M]$^+$ calcd for $C_{36}H_{37}N_2O_7P$, 640.23; found, 640.1). Anal. Calcd for $C_{36}H_{37}N_2O_7P$: C, 67.49; H, 5.82; N, 4.37. Found: C, 67.09; H, 6.16; N, 3.99.

Reaction with Functional Phosphonic Acid on ITO Surface

Synthesis of Compound for Reacting with a Functional Group: (E)-methyl 3-(4-(4,4,5,5,6,6,7,7,8,8,9,9,10,10,11,11,11-heptadecafluoroundecyloxy)phenyl)acrylate (E)-Methyl 3-(4-hydroxyphenyl)acrylate (166 mg, 0.93 mmol) was added to dry DMSO (10 mL) and stirred under nitrogen in a round bottom flask. Crushed sodium hydroxide (44 mg, 1.1 mmol) was added. After 30 minutes, 1,1,1,2,2,3,3,4,4,5,5,6,6,7,7,8,8-heptadecafluoro-11-iodoundecane (500 mg, 0.85 mmol) was added. The reaction was allowed to stir overnight. Washed with water and extracted with dichloromethane to yield an oil. This crude product was purified on a silica column using hexanes with increasing amounts of ethyl acetate as the eluent. A white solid was isolated (418 mg, 77% yield). $^1H$ NMR (400.14 MHz, $CDCl_3$) δ 7.65 (d, J=16.0 Hz), 7.48 (d, J=8.75 Hz, 2H), 6.90 (d, J=8.75 Hz, 2H), 6.32 (d, J=16.0 Hz), 4.07 (t, J=5.90 Hz, 2H), 3.80 (3H), 2.40-2.20 (m, 2H), 2.18-2.05 (m, 2H).

Modification of ITO with (E)-11-(cinnamoyloxy)undecylphosphonic acid and crosslinking to the surface. An ITO (on glass) substrate was washed with Triton-X 100 with a lens cloth. The substrate was then sonicated in Triton-X 100 solution for 10 minutes, rinsed with water, sonicated for 10 minutes in water, washed with ethanol, and then sonicated for 10 minutes in ethanol, then washed with ethanol and dried under nitrogen. The substrate was cut into two pieces so as multiple samples could be obtained from the same substrate. All samples were subjected to air plasma (15 minutes). 1 sample was immersed horizontally in a 1 mM solution of (E)-11-(cinnamoyloxy)undecylphosphonic acid in ethanol for several hours, until the volume of the liquid was below the level of the substrate. The other sample was immersed horizontally in ethanol for several hours, until the volume of the liquid was below the level of the substrate. They were then rinsed with ethanol and put into a 140° C. oven for 36 hours. They were then sonicated for 30 minutes in a 5% v/v solution of TEA/ethanol. It was then rinsed with ethanol, then water, and dried under nitrogen.

Solution Z—a solution of (E)-methyl 3-(4-(4,4,5,5,6,6,7,7,8,8,9,9,10,10,11,11,11-heptadecafluoroundecyloxy)phenyl)acrylate (7 mg) in dichloromethane (0.5 mL).

Sample 1—Modified ITO substrate, some of Solution Z dripped on, put in photoreactor for 10 minutes (8 bulbs—300 nm, 8 bulbs—350 nm), then rinsed with dichloromethane, sonicated in dichloromethane for 1 minute, then rinsed again in dichloromethane.

Sample 2—Modified ITO substrate, some of Solution Z dripped on, put in photoreactor for 30 minutes (8 bulbs—300 nm, 8 bulbs—350 nm), then rinsed with dichloromethane, sonicated in dichloromethane for 1 minute, then rinsed again in dichloromethane.

Elemental analysis of the surface showed the presence of fluorine for Sample 1 and Sample 2.

Modification of ITO with 3,3,4,4,5,5,6,6,7,7,8,8,8-tridecafluorooctylphosphonic acid An ITO (on glass) substrate were washed with Triton-X 100 with a lens cloth. The two substrates were then sonicated in Triton-X 100 solution for 10 minutes, rinsed with water, sonicated for 10 minutes in water, washed with ethanol, and then sonicated for 10 minutes in ethanol, then washed with ethanol and dried under nitrogen (the DSC method of Table 2). The substrate was cut into smaller pieces so as multiple samples could be obtained from the same substrate.

ITO—This substrate was immersed horizontally in ethanol for several hours, until the volume of the liquid was below the level of the substrate. It was then rinsed with ethanol, then water, and dried under nitrogen.

PA/ITO 0—This substrate was immersed horizontally in a 1 mM solution of 3,3,4,4,5,5,6,6,7,7,8,8,8-tridecafluorooctylphosphonic acid in ethanol for several hours, until the volume of the liquid was below the level of the substrate. It was then rinsed with ethanol, then water, and dried under nitrogen.

PA/ITO TEA 10—This substrate was immersed horizontally in a 1 mM solution of 3,3,4,4,5,5,6,6,7,7,8,8,8-tridecafluorooctylphosphonic acid in ethanol for several hours, until the volume of the liquid was below the level of the substrate. The substrate was then sonicated for 10 minutes in a 5% v/v solution of TEA/ethanol. It was then rinsed with ethanol, then water, and dried under nitrogen.

PA/ITO TEA 30—This substrate was immersed horizontally in a 1 mM solution of 3,3,4,4,5,5,6,6,7,7,8,8,8-tridecafluorooctylphosphonic acid in ethanol for several hours, until the volume of the liquid was below the level of the substrate. The substrate was then sonicated for 30 minutes in a 5% v/v solution of TEA/ethanol. It was then rinsed with ethanol, then water, and dried under nitrogen.

PA/ITO TEA 60—This substrate was immersed horizontally in a 1 mM solution of 3,3,4,4,5,5,6,6,7,7,8,8,8-tridecafluorooctylphosphonic acid in ethanol for several hours, until the volume of the liquid was below the level of the substrate. The substrate was then sonicated for 60 minutes in a 5% v/v solution of TEA/ethanol. It was then rinsed with ethanol, then water, and dried under nitrogen.

PA/ITO THF 10—This substrate was immersed horizontally in a 1 mM solution of 3,3,4,4,5,5,6,6,7,7,8,8,8-tridecafluorooctylphosphonic acid in ethanol for several hours, until the volume of the liquid was below the level of the substrate. The substrate was then sonicated for 10 minutes in THF. It was then rinsed with ethanol, then water, and dried under nitrogen.

PA/ITO THF 30—This substrate was immersed horizontally in a 1 mM solution of 3,3,4,4,5,5,6,6,7,7,8,8,8-tridecafluorooctylphosphonic acid in ethanol for several hours, until the volume of the liquid was below the level of the substrate. The substrate was then sonicated for 30 minutes in THF. It was then rinsed with ethanol, then water, and dried under nitrogen.

PA/ITO THF 60—This substrate was immersed horizontally in a 1 mM solution of 3,3,4,4,5,5,6,6,7,7,8,8,8-tridecafluorooctylphosphonic acid in ethanol for several hours, until the volume of the liquid was below the level of the substrate. The substrate was then sonicated for 60 minutes in THF. It was then rinsed with ethanol, then water, and dried under nitrogen.

PA/ITO THF 10+10—This substrate was immersed horizontally in a 1 mM solution of 3,3,4,4,5,5,6,6,7,7,8,8,8-tridecafluorooctylphosphonic acid in ethanol for several hours, until the volume of the liquid was below the level of the substrate. The substrate was then sonicated for 10 minutes in THF. The THF was discarded and the substrate was sonicated in THF for 10 minutes more. It was then rinsed with ethanol, then water, and dried under nitrogen.

Synthesis of Poly(PEG)(Phosphonic Acid) Copolymer

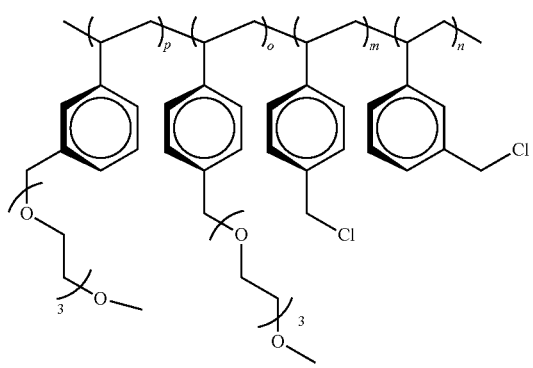

(o + p) : (m + n) = 9:1

Triethylene glycolmonomethylether (1.33 mL, 8.35 mmol) was dissolved in dry THF and allowed to stir under nitrogen. Sodium hydride (224 mg, 9.34 mmol) was added and the reaction allowed to stir for 30 minutes more. Poly (vinylbenzyl chloride) (1.50 g, 9.83 mmol) was then added and the reaction was allowed to stir overnight. The solvent was removed and the residue re-dissolved in ethyl acetate and washed with water. The solvent was removed under vacuum to yield the PEG/Cl polystyrene an orange sticky oil/solid (2.34 g).

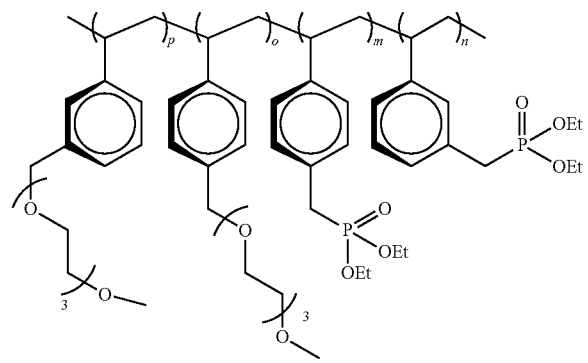

(o + p) : (m + n) = 9:1

The PEG/Cl polystyrene (500 mg, 1.78 mmol) was combined with triethylphosphite (0.30 mL, 1.78 mmol) in dioxane (15 mL) and the mixture was heated at 100° C. overnight, followed by stirring at 135° C. for 8 hours. After cooling, the reaction mixture was dripped into cold hexanes (~200 mL) while stirring vigorously. The hexanes were poured off and the sticky solid at the bottom re-dissolved in a minimal amount of ethyl acetate and then re-precipitated again into cold hexanes (~200 mL). The hexanes were poured off leaving a sticky yellow solid/oil of the PEG/phosphonate polystyrene on the bottom (482 mg).

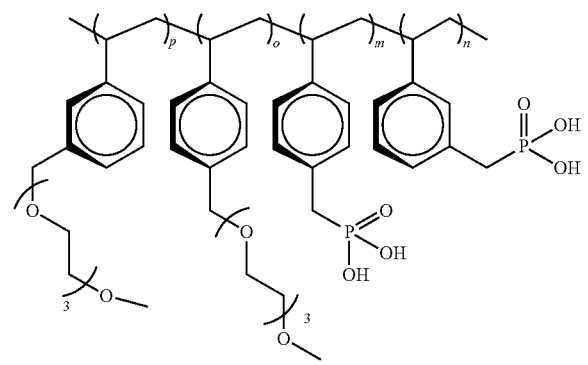

(o + p) : (m + n) = 9:1

The PEG/phosphonate polystyrene was dissolved in dry dichloromethane (20 mL). Bromotrimethylsilane (1.0 mL, excess mmol) was added via syringe. The reaction was capped with a greased glass stopper and allowed to stir for 6 hours. The volatiles were removed under reduced pressure to yield a yellow oil/solid. To this was added 1:1 methanol:water (25 mL) and the reaction allowed to reflux for 8 hours. After removing the solvents, the solid was put under high-vacuum to yield the PEG/phosphonic acid polystyrene as a soft off-white solid (260 mg).

Synthesis of Potassium Phosphonates

Synthesis of Potassium hydrogenoctadecylphosphonate (octadecylphosphonic acid monobasic potassium salt).

3.0 mL of a 100 mM solution of KOH was titrated into a dispersed solution of octadecylphosphonic acid (100 mg, 0.3 mmol) in 30 mL of water while stirring. The mixture was then heated to 60° C. while stirring until the water was evaporated (about 3 hours). The resulting white solid was then dried under vacuum.

Synthesis of Potassium octadecylphosphonate (octadecylphosphonic acid dibasic potassium salt)

6.0 mL of a 100 mM solution of KOH was titrated into a dispersed solution of octadecylphosphonic acid (100 mg, 0.3 mmol) in 30 mL of water while stirring. The mixture was then heated to 60° C. while stirring until the water was evaporated (about 3 hours). The resulting white solid was then dried under vacuum.

Synthesis of Phosphonic Acids

Figure 18:
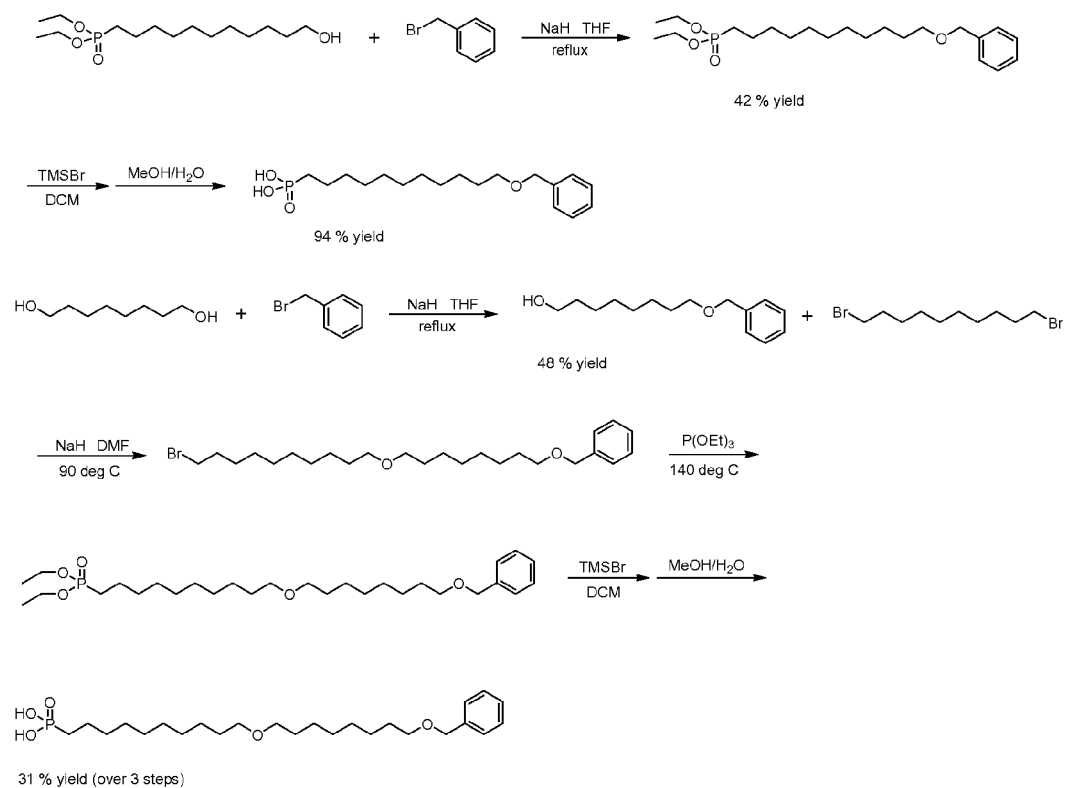
FIG. 18 outlines the synthesis of a phosphonic acid.
Figure 19:
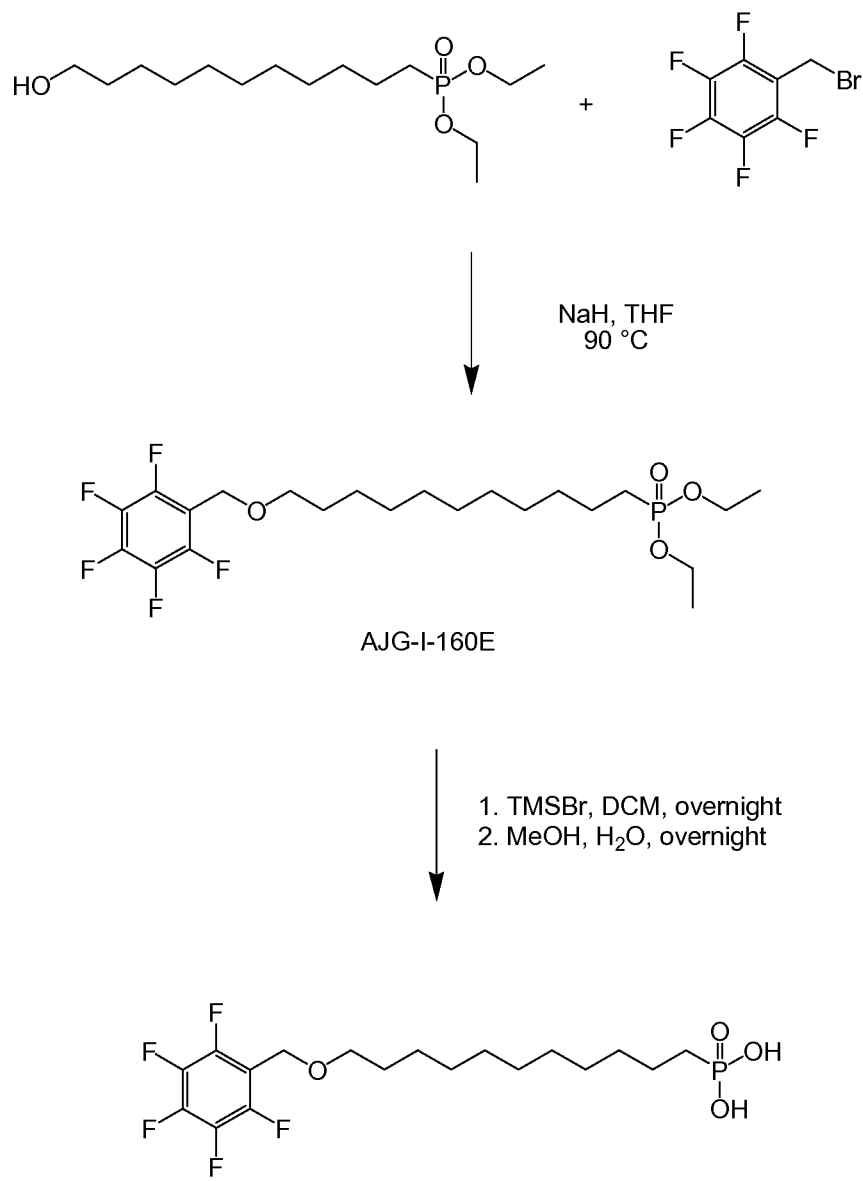
FIG. 19 outlines the synthesis of a phosphonic acid.
Figure 20:
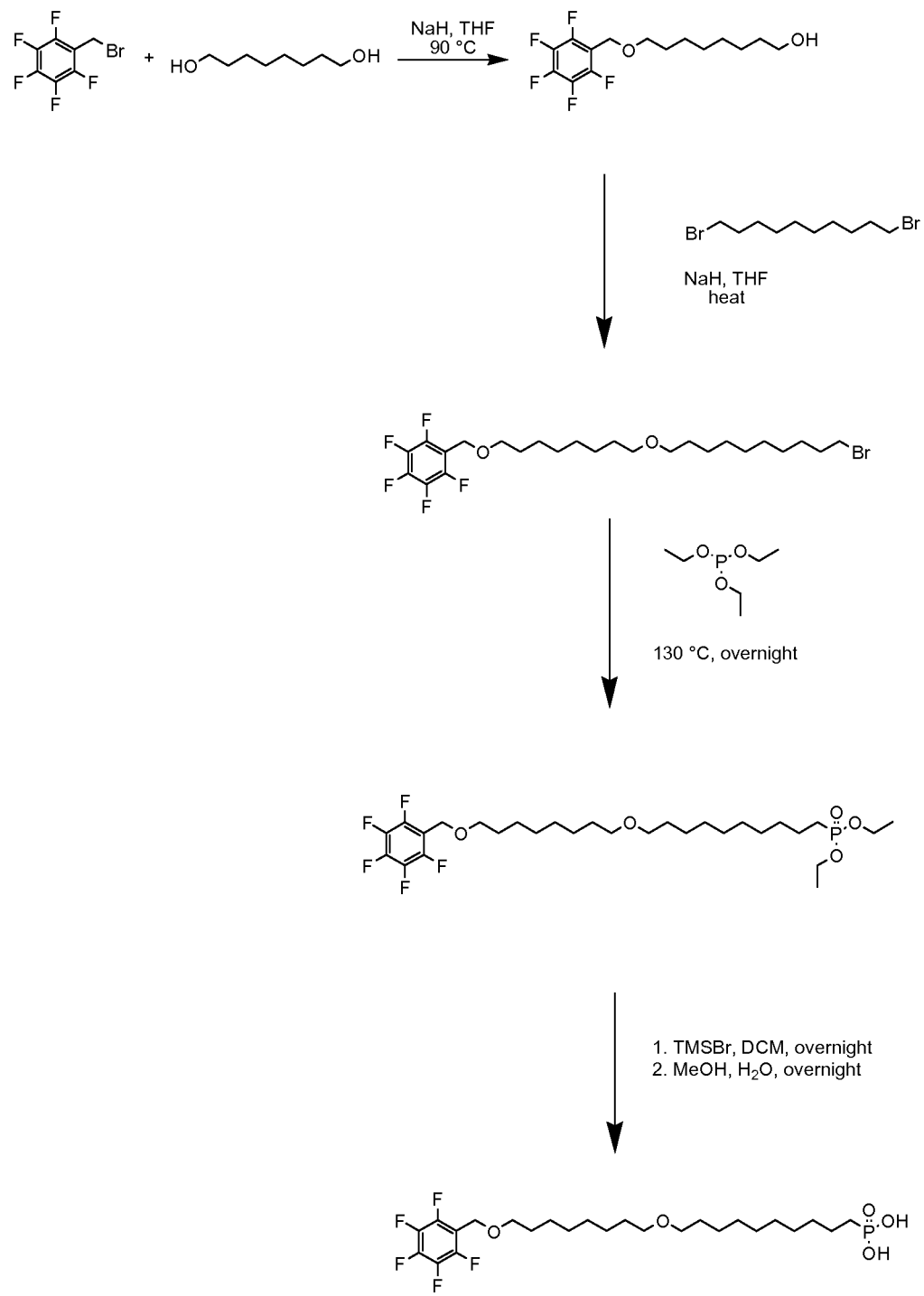
FIG. 20 outlines the synthesis of a phosphonic acid.

The following synthesis is generically described in FIG. 18.

Diethyl 11-(benzyloxy)undecylphosphonate

Diethyl 11-hydroxyundecylphosphonate (4.0 g, 13.0 mmol) and 18-crown-6 (spatula tip) were added to anhydrous tetrahydrofuran under inert atmosphere. Sodium hydride (312 mg, 13.0 mmol) was added and the solution allowed to stir for 10 minutes. Benzyl bromide (2.4 mL, 19.5 mmol) was then added and the reaction stirred at reflux for 4 hours. After cooling to room temperature, dichloromethane was added and the mixture washed with water and brine. The organic layer was collected, dried over magnesium sulfate, and concentrated under reduced pressure to yield a liquid. Column chromatography (stationary phase:silica, mobile phase:ethyl acetate) was used to isolate the desired product ($R_f$=0.70, ethyl acetate) as a clear oil (2.173 g, 42% yield). $^1$H NMR (500.13 MHz, $CD_2Cl_2$) δ 7.36-7.29 (m, 4H), 7.29-7.23 (m), 4.47 (2H), 4.10-3.97 (m, 4H), 3.45 (t, J=6.62 Hz, 2H), 1.72-1.62 (m, 2H), 1.62-1.48 (m, 4H), 1.40-1.20 (m, 20H). $^{13}C\{^1H\}$ NMR (100.62 MHz, $CD_2Cl_2$) δ 139.4, 128.6 (2C), 127.9 (2C), 127.7, 73.03, 70.88, 61.57 (d, J=6.4 Hz, 2C), 30.95 (d, J=16.8 Hz), 30.17, 29.94, 29.91, 29.85, 29.75, 29.48, 26.58, 25.91 (d, J=139.8 Hz), 22.78 (d, J=5.3 Hz), 16.68 (d, J=5.9 Hz, 2C). $^{31}P\{^1H\}$ NMR (202.45 MHz, $CD_2Cl_2$): δ 32.83. Analysis calculated (found) %: C 66.30 (65.66), H 9.86 (9.95). MS (ESI, m/z): 399 ($M^+$, 100%). Exact mass calculated (found) for $[M+H]^+$, m/z): 399.2659 (399.2671).

11-(benzyloxy)undecylphosphonic acid

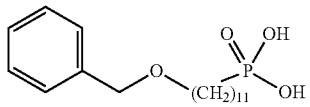

PA-1

Diethyl 11-(benzyloxy)undecylphosphonate (1.00 g, 2.51 mmol) was dissolved in dry dichloromethane (20 mL). Bromotrimethylsilane (1.1 mL, 8.28 mmol) was added via syringe. The reaction was capped with a greased glass stopper and allowed to stir overnight. The volatiles were removed under reduced pressure to yield a yellow oil. This was dissolved in 5:1 methanol:water (20 mL) and allowed to stir 4 hours more. After concentration of the organic, the viscous yellow oil was dissolved in hot acetonitrile and a white crystalline solid was obtained (806 mg, 94% yield). $^1$H NMR (400.14 MHz, DMSO) δ 7.40-7.20 (m, 5H), 4.43 (2H), 3.39 (t, J=6.49 Hz, 2H), 1.60-1.33 (m, 6H), 1.33-1.15 (m, 14H). $^{13}$C{$^1$H} NMR (100.62 MHz, DMSO) δ 138.7, 128.2 (2C), 127.4 (2C), 127.3, 71.79, 69.59, 30.09 (d, J=15.9 Hz), 29.21, 29.04, 29.01, 28.89, 28.87, 28.73, 27.53 (d, J=136.6 Hz), 25.72, 22.72 (d, J=4.6 Hz). $^{31}$P{$^1$H} NMR (161.97 MHz, DMSO): δ 27.71. Analysis calculated (found) %: C 63.14 (62.87), H 9.13 (9.13). MS (ESI, m/z): 341 (M⁻, 100%). Exact mass calculated (found) for [M−H]⁻, m/z): 341.188722 (341.189600).

Diethyl 10-(8-(benzyloxy)octyloxy)decylphosphonate

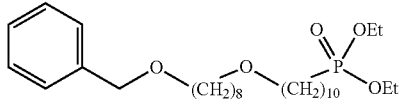

1,8-octanediol (5.0 g, 34.2 mmol) and 18-crown-6 (spatula tip) were added to anhydrous tetrahydrofuran under inert atmosphere. Sodium hydride (820 mg, 34.2 mmol) was added and the solution stirred for 10 minutes. Benzyl bromide (4.1 mL, 34.2 mmol) was then added and the reaction stirred at reflux for 4 hours and then overnight at room temperature. A white precipitate formed and this was filtered off. The filtrate was concentrated under reduced pressure. Column chromatography (stationary phase:silica, mobile phase:1:1 hexanes:ethyl acetate) was used to isolate the desired product ($R_f$=0.40, 1:1 hexanes:ethyl acetate) as a yellow oil (3.914 g, 48% yield). $^1$H NMR is consistent with 8-(benzyloxy)octan-1-ol.

8-(benzyloxy)octan-1-ol (1.15 g, 4.86 mmol) was added to anhydrous dimethylformamide in a round bottom flask under inert atmosphere. Sodium hydride (175 mg, 7.3 mmol) was added and the solution allowed to stir for 30 minutes. 1,10-dibromodecane (11.7 g, 38.9 mmol) was then added and the reaction stirred at 90° C. for 4 hours and then cooled to room temperature. The solvent was removed under reduced pressure. Column chromatography (stationary phase:silica, mobile phase:hexanes with increasing amounts of ethyl acetate) was used to isolate the desired product ($R_f$=0.65, 9:1 hexanes:ethyl acetate) as a viscous oil. The resulting oil contained some desired product (((8-(10-bromodecyloxy)octyloxy)methyl)benzene, as evidenced by $^1$H NMR), though impure (tlc), and used in the next reaction without further purification.

((8-(10-bromodecyloxy)octyloxy)methyl)benzene (900 mg, 2.0 mmol) was combined with triethylphosphite (5 mL, 30 mmol) and the reaction mixture stirred at 135° C. for 2 days. Excess triethylphosphite and other side products were removed under vacuum (approximately 0.1 torr) and with heating at 80° C. for 5 hours to yield a viscous oil (760 mg, 74% yield). $^1$H NMR (400.14 MHz, CD$_2$Cl$_2$) δ 7.35-7.29 (m, 4H), 7.29-7.21 (m), 4.46 (2H), 4.13-3.92 (m, 4H), 3.45 (t, J=6.60 Hz, 2H), 3.35 (t, J=6.66 Hz, 4H), 1.73-1.62 (m, 2H), 1.62-1.41 (m, 8H), 1.41-1.18 (m, 26H). $^{13}$C{$^1$H} NMR (100.62 MHz, CD$_2$Cl$_2$) δ 139.4, 128.6 (2C), 127.9 (2C), 127.7, 73.02, 71.13 (2C), 70.87, 61.61 (d, J=6.4 Hz, 2C), 30.94 (d, J=16.8 Hz), 30.17 (2C), 30.14, 29.91, 29.84, 29.81 (2C), 29.72, 29.45, 26.57, 26.53 (2C), 25.87 (d, J=140.3 Hz), 22.76 (d, J=5.2 Hz), 16.65 (d, J=5.9 Hz, 2C). $^{31}$P{$^1$H} NMR (161.97 MHz, CD$_2$Cl$_2$): δ 32.94. Analysis calculated (found) %: C 67.94 (67.08), H 10.42(10.50). MS (ESI, m/z): 513 (M⁺, 100%). Exact mass calculated (found) for [M+H]⁺, m/z): 513.3703 (513.3674).

Synthesis of
10-(8-(Benzyloxy)octyloxy)decylphosphonic acid
(PA-2)

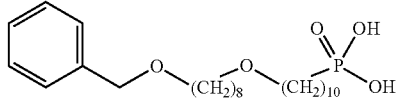

PA-2

Diethyl 10-(8-(benzyloxy)octyloxy)decylphosphonate (680 mg, 1.33 mmol) was dissolved in dry dichloromethane (15 mL). Bromotrimethylsilane (0.53 mL, 4.05 mmol) was added via syringe. The reaction was capped with a greased glass stopper and stirred overnight. The volatiles were removed under reduced pressure to yield a yellow oil. This was dissolved in 5:1 methanol:water (10 mL) and stirred 4 hours more. After concentration of the organic, the viscous yellow oil was recrystallized in acetonitrile to yield a white crystalline solid (590 mg, 98% yield). $^1$H NMR (400.14 MHz, DMSO) δ 7.40-7.19 (m, 5H), 4.42 (2H), 3.39 (t, J=6.48 Hz, 2H), 3.29 (t, J=6.46 Hz, 4H), 1.58-1.34 (m, 10H), 1.34-1.10 (m, 20H). $^{13}$C{$^1$H} NMR (100.62 MHz, DMSO) δ 138.7, 128.2 (2C), 127.3 (2C), 127.3, 71.79, 69.91 (2C), 69.59, 30.11 (d, J=16.0 Hz), 29.25, 29.21, 29.20, 29.05, 28.89 (2C), 28.84 (2C), 28.73, 27.55 (d, J=136.5 Hz), 25.76, 25.69, 25.67, 22.74 (d, J=4.5 Hz). $^{31}$P{$^1$H} NMR (161.97 MHz, DMSO): δ 27.74. Analysis calculated (found) %: C 65.76 (65.79), H 9.93 (10.00). MS (ESI, m/z): 455 (M⁻, 100%). Exact mass calculated (found) for [M−H]⁻, m/z): 455.2932 (455.2932).

Evaluation of Electrodes Modified with Phosphonic Acid Dialectric Monolayers

The PA-1 and PA-2 Phosphonic acids were evaluated as potential monolayer dielectrics on metal oxide electrode surfaces.

Aluminium metal electrodes (~30 nm thick) were thermally evaporated under high vacuum (10⁻⁶ mbar) employing shadow masks. The surfaces of the Al electrodes were subsequently oxidized at high temperatures (300° C.) by spraying them with deionized water. An oxygen plasma step (30 sec at 80W) was then applied following thermal oxidation, to form Al/AlOx electrodes.

The Al/AlOx electrodes were then submerged in a 1 mM solution of the phosphonic acids PA-1 or PA-2 in ethanol for several hours (>10h). Alternatively the SAM solution can be applied three times by spin-coating. Substrates were then sonicated in ethanol followed by thermal annealing at 145° C. for >12 hours.

The presence of PA-1 on the electrode surfaces was confirmed by contact angle measurements (See Wobkenberg et al, Applied Physics Letters 93, 013303 2008, incorporated by reference herein) using a Krüss DSA100 drop shape analysis system. The surface energy components of PA-1 were measured to be $\gamma_s^D=47.7$ mN/m and $\gamma_s^P=0.1$ mN/m using the Owens-Wendt-Kaelble method. The surface energy characteristics of Al/AlOx/PA-2 are under investigation. A summary of the contact angle images (Al/AlOx/PA-1) and surface energies of the various liquids used are shown in Table 5.

Figure 21:
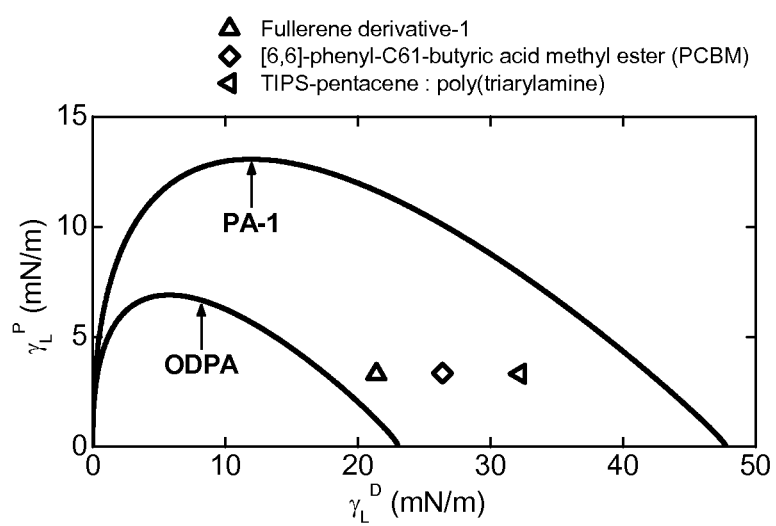
FIG. 21 shows wetting envelops (θ=0°) for Al/AlOx surfaces functionalized with ODPA and PA-1.

Using the experimentally obtained data from Table 5, the $\theta=0°$ wetting envelope for PA-1 functionalized Al/AlOx surface were calculated and plotted together with and compared with the $\theta=0°$ wetting envelope for use of ODPA (Octadecylphosphonic acid, $CH_3(CH_2)_{17}PO(OH)_2$) in a similar manner (See Wöbkenberg et al, Applied Physics Letters 93, 013303 2008, incorporated by reference herein). FIG. 21 shows the wetting envelopes of Al/AlOx electrodes functionalized with PA-1 and PA-2 (solid lines), together with the surface energy co-ordinates of various small molecule semiconductor solutions (symbols). The latter co-ordinates were taken from Wöbkenberg P. H. et al., Appl. Phys. Lett. 93, 013303 (2008).

From FIG. 21 it is clear that surfaces modified with the PA-1 phosphonic acid exhibits a much larger wetting envelope and hence much improved wetability for organic molecules as compared to ODPA. It is worth noting that all the small molecule semiconductors shown in the inset of FIG. 21 form good quality thin films when spin coat onto the PA-1 and PA-2 functionalized Al/AlOx electrodes.

Figure 22:
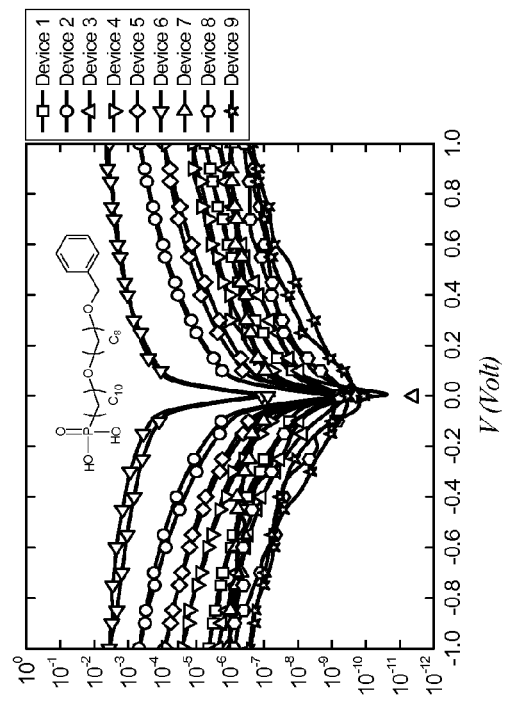
FIG. 22 shows current/voltage characteristics obtained from Al/AlOx/SAM/Au structures having the electrodes modified with PA-1 and PA-2.
Figure 22:
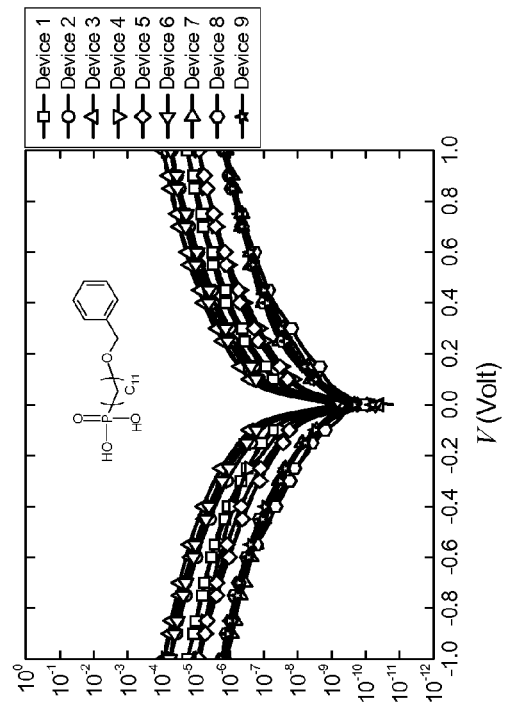

The current-voltage (I-V) characteristics of PA-1 and PA-2 modified electrodes were also investigated. Representative sets of I-V measurements for Al/AlOx/SAM/Au capacitors (which are effectively a metal/insulator/metal structure) are shown in FIG. 22. The rather large spread of the current vs bias for both types of devices (particularly PA-2 based devices) is attributed to the specific preparation conditions and can likely be improved by functionalization process optimization.

Figure 23:
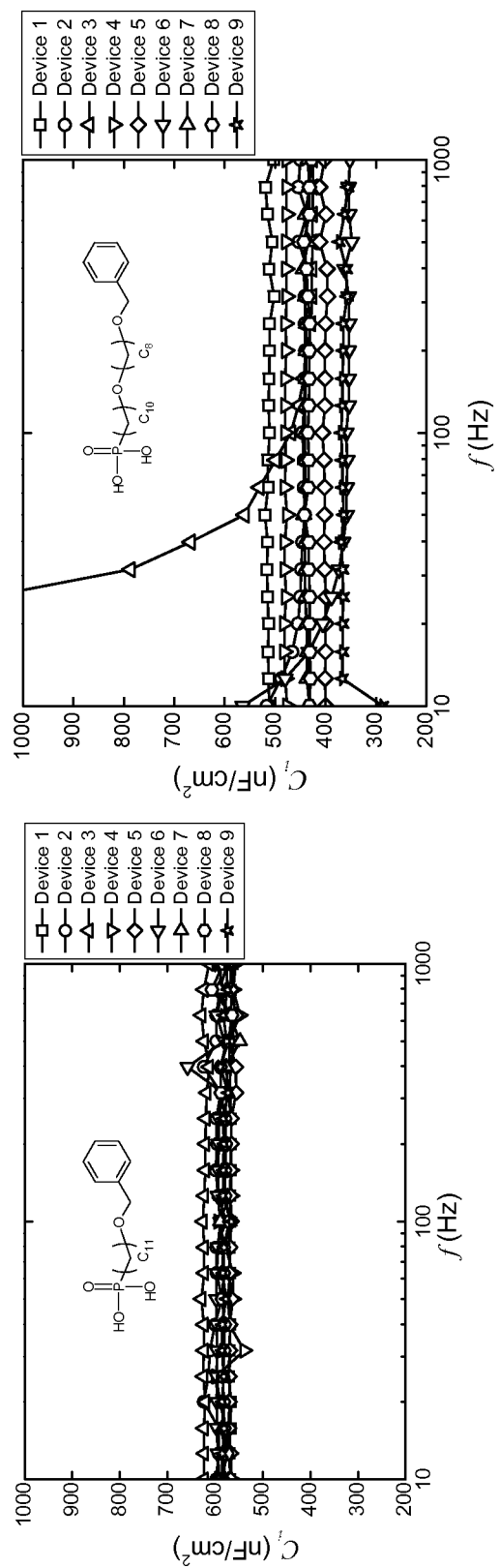
FIG. 23. Geometrical capacitance of the Al/AlOx/SAM/Au (SAM=PA-1 or PA-2) as a function of small AC signal frequency.
Figure 24:
FIG. 24 shows surface energy measurements of PA-1 functionalized Al/AlOx surfaces.
Figure 24:
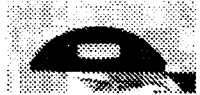
Figure 24:

The geometrical capacitances (F/cm$^2$) of the Al/AlOx/SAM/Au structures were also measured (See FIG. 23) and used for the calculation of the charge carrier mobility SAM based OFETs. A general observation is that $C_i$ is, as expected, larger (~600 nF/cm$^2$) for devices based on the PA-1 than devices based on PA-2 (350-500 nF/cm$^2$).

Synthesis of
11-(perfluorophenoxy)undecylphosphonic acid

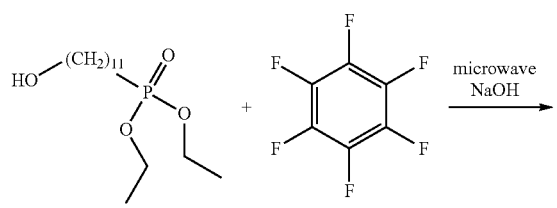

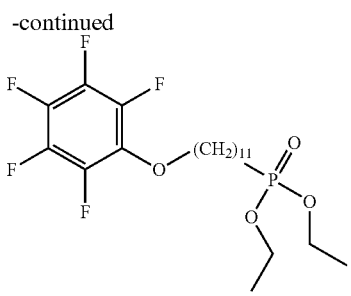

1. TMSBr, DCM, overnight
2. MeOH, H$_2$O, overnight

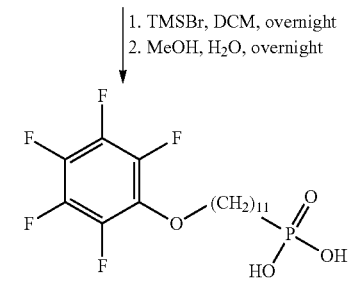

In a microwave tube under a flow of nitrogen was combined hexafluorobenzene (1.97 g, 10.6 mmol), diethyl 11-hydroxyundecylphosphonate (4.23 g, 13.7 mmol), and solid sodium hydroxide (0.85 g, 21.3 mmol). The vessel was sealed and irradiated in a CEM Discover microwave ramping to 135° C. and holding that temperature for 2 minutes. The resulting yellow mixture was poured into water, acidified with 1 M HCl, and extracted with ether. The organic layer was washed three times each with dilute aqueous sodium hydroxide, water, brine, and dried over magnesium sulfate. Volatiles were removed under reduced pressure to afford a slightly yellow, viscous oil which was purified by column chromatography packed with silica gel (1:1 chloroform:ethyl acetate) to afford diethyl 11-hydroxyundecylphosphonate (1.71 g, 34%).

$^1$H NMR (399.9 MHz, CDCl$_3$) δ 4.06 (m, 6H), 1.73 (m, 4H), 1.57 (m, 2H), 1.37 (m, 20H). $^{13}$C{$^1$H} NMR (125.8 MHz, CDCl$_3$) δ 141.7 (d, J=248.6 Hz), 138.9 (d, J=101.3 Hz), 136.6 (d, J=111.1 Hz,), 133.7 (d, J=4.5 Hz), 75.8, 61.3 (d, J=6.5Hz), 30.6 (d, J=17.0 Hz), 29.8, 29.4, 29.2, 29.1, 29.0, 26.2, 25.4, 25.1, 22.4 (d, J=2.6 Hz). $^{31}$P{$^1$H} NMR (161.91 MHz, CDCl$_3$): δ 33.30. $^{19}$F NMR (376.3 MHz, CDCl$_3$): δ −155.86 (m, 2F), −162.44 (m, 2F), 162.81 (m, 1F), from trifluoro acetic acid. EI-MS exact mass calculated (found) for M$^+$: 474.1958 (474.1951). Analysis calculated (found) %: C 53.16 (52.98), H 6.80 (6.97), F 20.02 (19.79). Exact mass calculated (found) for [M+H]$^+$, m/z: 474.1958 (474.1951).

A solution of diethyl 11-hydroxyundecylphosphonate (1.01 g, 2.1 mmol) in 15 mL of dry dichloromethane and 1.1 mL (8.3 mmol) of bromotrimethylsilane was made. The system was sealed with a greased stopper and allowed to stir overnight. Volatiles were removed under reduced pressure to produce a viscous, brown oil, which was dissolved in 20 mL of a 4:1 methanol:water solution and allowed to stir for six hours. After removal of solvent under reduced pressure an off white solid formed, which was recrystallized from acetonitrile to afford while crystals of 11-(perfluorophenoxy)undecylphosphonic acid (0.84 g, 94%). $^1$H NMR (399.9 MHz, DMSO-d$^6$) δ 4.17 (t, J=1.20 Hz, 2H), 1.69 (m, 2H), 1.50-1.25 (m, 18H). $^{13}$C{$^1$H} NMR (100.5 MHz, DMSO-d$^6$) δ 75.5, 30.0 (d, J=16.0 Hz), 29.1, 28.9, 28.8, 28.6, 28.5, 28.1, 26.8, 24.9, 22.6 (d, J=4.5 Hz) aromatic carbons not observed due to strong fluorine coupling. $^{31}$P{$^1$H} NMR (161.91 MHz, DMSO-d6): δ 27.71. 19F NMR (376.3 MHz, DMSO-d6): δ 155.47 (m, 2F), 162.20 (m, 2F), 162.82 (m, 1F), from trifluoro acetic acid. Analysis calculated (found) %: C 48.81 (48.95), H 5.78(5.68), F 22.71 (22.76).

Synthesis of
11-(perfluorobenzyloxy)undecylphosphonic acid

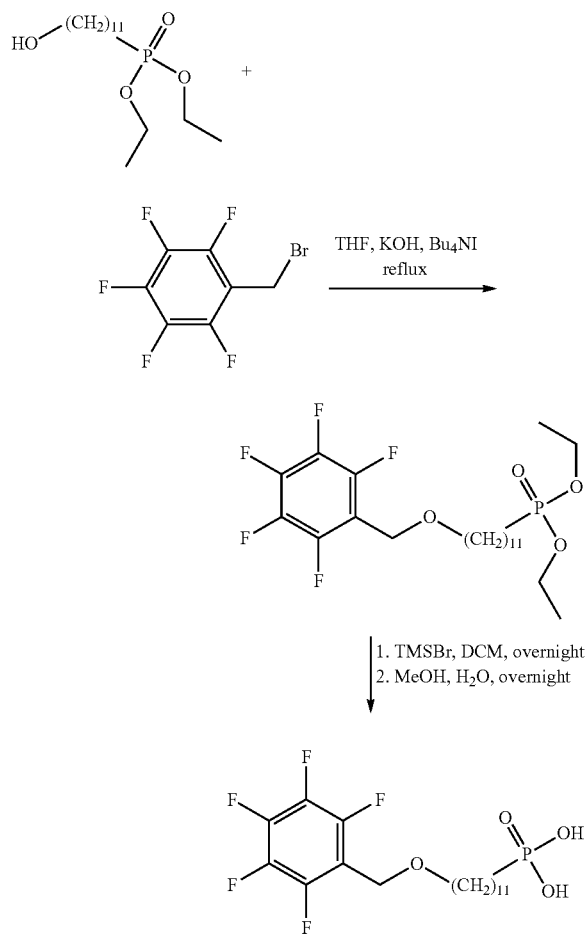

Under an inert atmosphere was combined potassium hydroxide (0.57 g, 10.2 mmol), pentafluorobenzylbromide (1.4 mL, 9.95 mmol), diethyl 11-hydroxyundecylphosphonate (3.05 g, 9.89 mmol), and tetrabutylammonium iodide (0.01 g, 0.03 mmol) with anhydrous THF. The mixture was allowed to stir at 65° C. for approximately 9 hours and filtered through a thin layer of silica gel, eluting with THF. Volatiles were removed under reduced pressure and the reaction mixture was distilled utilizing Kugelrohr distillation (0.18 Torr, 250° C.) to afford impure diethyl 11-(perfluorobenzyloxy)undecylphosphonate. The impure material was subsequently purified by column chromatography packed with silica gel (hexane:ethyl acetate gradient) to afford 0.91 g (19%) of diethyl 11-(perfluorobenzyloxy)undecylphosphonate.

1H NMR (399.9 MHz, CDCl3) δ 4.56 (t, J=1.8 Hz, 2H), 4.08 (m, 4H), 3.47 (t, J=6.6 Hz, 2H), 1.73-1.24 (m, 26H). 13C{1H} NMR (125.8 MHz, CDCl3) δ 145.6 (d, J=246.4 Hz), 141.2 (d, J=261.8 Hz), 137.3 (d, J=270.7 Hz), 111.5, 71.1, 61.3 (d, J=6.5 Hz), 59.4, 32.8, 30.7, 30.5, 29.5, 29.3, 29.0, 26.2, 25.9, 25.1, 22.4 (d, J=5.3 Hz), 16.4 (d, J=6.0 Hz). Analysis calculated (found) %: C 54.09 (54.30), H 7.02 (7.07), F 19.45, 19.16). Exact mass calculated (found) for [M+H]+, m/z: 488.2115 (488.2115).

A solution of diethyl 11-(perfluorobenzyloxy)undecylphosphonate (0.63 g, 1.3 mmol) in 15 mL of dry dichloromethane and 0.7 mL (5.3 mmol) bromotrimethylsilane was made. The system was sealed with a greased stopper and allowed to stir overnight. Volatiles were removed under reduced pressure to produce a viscous, brown oil, which was dissolved in 25 mL of a 4:1 methanol:water solution and allowed to stir for six hours. After removal of solvent under reduced pressure an off white solid formed, which was recrystallized from a minimal amount of acetonitrile to afford white crystals of 11-(perfluorobenzyloxy)undecylphosphonic acid (0.49 g, 92%). 1H NMR (399.9 MHz, DMSO-d6) δ 4.55 (s, 2H), 3.42 (t, J=6.4 Hz, 2H), 1.49-1.44 (m, 6H), 1.34-1.18 (m, 14H). 13C{1H} NMR (100.5 MHz, DMSO-d6) δ 104.5, 69.9, 58.8, 30.1, 29.9, 28.9, 28.8, 28.8, 28.7, 28.1, 26.8, 25.4, 22.648 (d, J=4.8 Hz). 31P{1H} NMR (161.91 MHz, DMSO-d6): δ 27.63. 19F NMR (376.3 MHz, DMSO-d6): δ −141.86 (m, 2F), −152.95 (m, 1F), −160.88 (m, 2F), from trifluoro acetic acid. Analysis calculated (found): C 50.00 (50.16), H 6.06 (6.23), F 21.97 (21.79). Exact mass calculated (found) for [M−H]−, m/z: 432.1489 (432.1487).

Other embodiments are within the following claims.

The invention claimed is:

1. A composition of matter comprising a molecule having the structure:

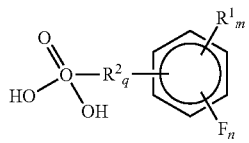

wherein: independently at each occurrence,

R1 is a halogen, an alkyl group, a heteroalkyl group, an aryl group, or a heteroaryl group;

R2 is —(CH2)x—Oy—(CH2)x—Oy—(CH2)z— wherein, independently at each occurrence, x=1-12, y=0-1, and z=0-3, provided that R2 comprises from 3 to 30 —CH2— groups, and at least one ether linkage, n=1-5, m=0-5, and q=1-3.

2. The composition of claim 1, wherein the composition comprises an electrode having a surface.

3. The composition of claim 2, wherein the phosphonic acid binding group of the molecule is bound to the electrode surface.

4. The composition of claim 1, wherein R2 is bonded to the phenyl ring through an ether.

5. A composition of matter comprising a molecule having the structure:

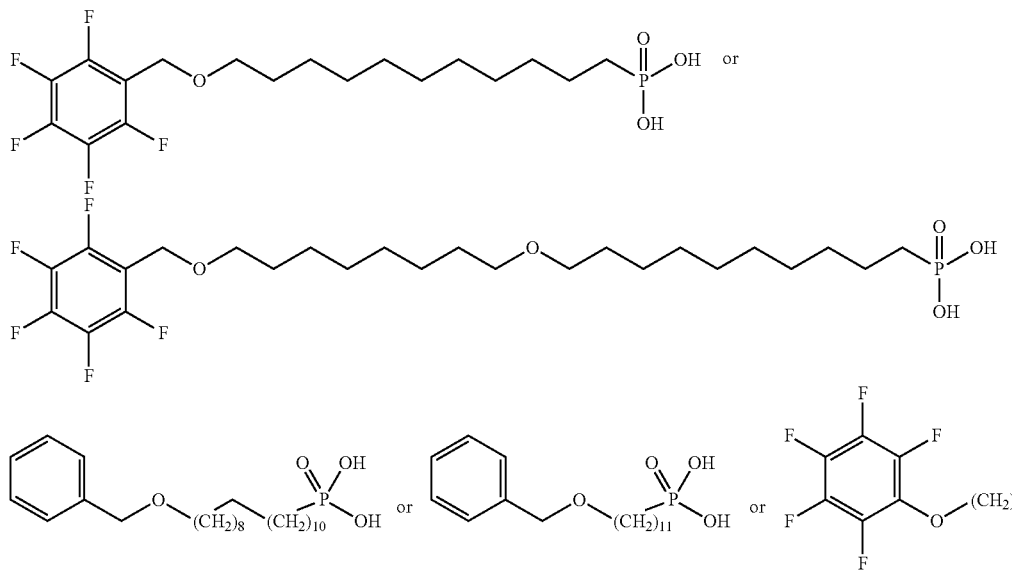

6. A device comprising the composition of claim 1.

7. The device of claim 6, wherein the phosphonic acid group binds covalently or non-covalently to the surface of a metal oxide.

8. The device of claim 7, wherein the molecule forms a monolayer on the metal oxide.

9. The device of claim 7, wherein the metal oxide surface is an electrode.

10. A device of claim 6 that is a transistor.

11. A method of modifying the surface energy of an electrode by depositing the composition of claim 1 on a surface of the electrode.

12. The method of claim 11, wherein the molecule binds to the electrode.

13. The method of claim 11 wherein the molecule forms a monolayer.

14. A device comprising the composition of claim 5.

15. The device of claim 14, where the phosphonic acid group binds covalently or non-covalently to the surface of a metal oxide.

16. The device of claim 15, wherein the modecule forms a monolayer on the metal oxide.

17. The device of claim 16, wherein the metal oxide surface is an electrode.

18. A device of claim 14 that is a transistor.

* * * * *